United States Patent
Sharma et al.

(10) Patent No.: US 7,307,063 B2
(45) Date of Patent: *Dec. 11, 2007

(54) MELANOCORTIN METALLOPEPTIDES FOR TREATMENT OF SEXUAL DYSFUNCTION

(75) Inventors: Shubh Sharma, Cranbury, NJ (US); Annette Shadiack, Somerset, NJ (US); Yi-Qun Shi, East Brunswick, NJ (US); Wei Yang, Edison, NJ (US); Hui-Zhi Cai, East Brunswick, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 336 days.

This patent is subject to a terminal disclaimer.

(21) Appl. No.: 10/640,755

(22) Filed: Aug. 13, 2003

(65) Prior Publication Data

US 2004/0038897 A1 Feb. 26, 2004

Related U.S. Application Data

(63) Continuation of application No. PCT/US02/04431, filed on Feb. 13, 2002.

(60) Provisional application No. 60/268,591, filed on Feb. 13, 2001.

(51) Int. Cl.
C07K 5/10 (2006.01)

(52) U.S. Cl. .......... 514/17; 530/327; 530/328; 530/329; 530/330; 514/2; 514/6; 514/16; 514/18; 556/1; 556/45

(58) Field of Classification Search .......... 530/327, 530/328, 329, 330; 514/2, 6, 16–18; 556/1, 556/45
See application file for complete search history.

(56) References Cited

U.S. PATENT DOCUMENTS

| | | | |
|---|---|---|---|
| 5,576,290 A | 11/1996 | Hadley | |
| 5,622,860 A | 4/1997 | Yamada et al. | |
| 5,639,778 A | 6/1997 | Andersson et al. | |
| 5,668,254 A | 9/1997 | Deghenghi | |
| 5,674,839 A | 10/1997 | Hruby et al. | |
| 5,693,608 A | 12/1997 | Bechgaard et al. | |
| 5,703,220 A | 12/1997 | Yamada et al. | |
| 5,710,265 A | 1/1998 | Yamada et al. | |
| 5,714,576 A | 2/1998 | Hruby et al. | |
| 5,731,408 A | 3/1998 | Hadley et al. | |
| 5,766,877 A | 6/1998 | Stark et al. | |
| 5,770,178 A | 6/1998 | Itaya et al. | |
| 5,837,521 A | 11/1998 | Cone et al. | |
| 5,891,418 A | 4/1999 | Sharma | |
| 5,908,609 A | 6/1999 | Lee et al. | |
| 5,908,825 A | 6/1999 | Fasano et al. | |
| 5,932,779 A | 8/1999 | Lee et al. | |
| 5,977,070 A | 11/1999 | Piazza et al. | |
| 5,994,087 A | 11/1999 | Cone et al. | |
| 6,027,711 A | 2/2000 | Sharma | |
| 6,048,527 A | 4/2000 | Granoff et al. | |
| 6,051,555 A | 4/2000 | Hadley | |
| 6,054,556 A | 4/2000 | Huby et al. | |
| 6,060,589 A | 5/2000 | Stark et al. | |
| 6,100,048 A | 8/2000 | Cone et al. | |
| 6,117,975 A | 9/2000 | Yamada et al. | |
| 6,126,916 A | 10/2000 | McBride et al. | |
| 6,127,381 A | 10/2000 | Basu et al. | |
| 6,210,942 B1 * | 4/2001 | Lewis et al. | 435/183 |
| 6,225,086 B1 * | 5/2001 | Morrow et al. | 435/69.1 |
| 6,689,813 B2 * | 2/2004 | Keri et al. | 514/565 |
| 2001/0009899 A1 | 7/2001 | Keri et al. | |
| 2001/0029259 A1 | 10/2001 | Nargund et al. | |
| 2002/0012948 A1 | 1/2002 | Sharma et al. | |

FOREIGN PATENT DOCUMENTS

| | | |
|---|---|---|
| WO | WO 98/10068 | 3/1998 |
| WO | WO 98/27113 | 6/1998 |
| WO | WO 98/56914 | 12/1998 |
| WO | WO 99/21571 | 5/1999 |
| WO | WO 99/43709 | 9/1999 |
| WO | WO 99/54358 | 10/1999 |
| WO | WO 99/55679 | 11/1999 |
| WO | WO 99/57148 | 11/1999 |
| WO | WO 99/64002 | 12/1999 |
| WO | WO 00/05263 | 2/2000 |
| WO | WO 00/06777 | 2/2000 |
| WO | WO 00/14115 | 3/2000 |

(Continued)

OTHER PUBLICATIONS

Fabris, D., et al., "Investigation of Zinc Chelation in Zinc-Finger Arrays by Electrospray Mass Spectrometry", *Inorganic Chemistry*, vol. 38, (1999),1322-1325.

Giblin, Michael F., et al., "Design and Characterization of 0-melanocortin Peptide Analogs Cyclized through Rhenium and Technetium Metal Coordination", *Proceedings of National Academy Science USA*, vol. 95, (Oct. 1998),12814-12818.

Shi, Yi-Qun, et al., "Conformationally Constrained Metallpeptide Template for Melanocortin-1 Receptor", *American Chemical Society, 218th ACS National Meeting, Abstracts of Papers, Part 1, Abstract MEDI 257*, (Aug. 22, 1999).

(Continued)

*Primary Examiner*—David Lukton
(74) *Attorney, Agent, or Firm*—Stephen A. Slusher

(57) ABSTRACT

Metallopeptides are provided for use in treatment of sexual dysfunction in mammals. The metallopeptides are agonists for at least one of melanocortin-3 or melanocortin-4 receptors. The metallopeptides are conformationally fixed on complexation of a metal ion-binding portion thereof with a metal ion. Also provided are metallopeptides that are antagonists for at least one of melanocortin-3 or melanocortin-4 receptors.

12 Claims, 4 Drawing Sheets

FOREIGN PATENT DOCUMENTS

| | | |
|---|---|---|
| WO | WO 00/33658 | 6/2000 |
| WO | WO 00/36136 | 6/2000 |
| WO | WO 00/39147 | 7/2000 |
| WO | WO 00/44898 | 8/2000 |
| WO | WO 00/53148 | 9/2000 |
| WO | WO 00/58361 | 10/2000 |
| WO | WO 00/74679 | 12/2000 |
| WO | WO 01/00224 | 1/2001 |
| WO | WO 01/05401 | 1/2001 |
| WO | WO 01/10842 | 2/2001 |
| WO | WO 01/13112 | 2/2001 |
| WO | WO 01/23392 | 4/2001 |
| WO | WO 01/30808 | 5/2001 |
| WO | WO 01/52880 | 7/2001 |
| WO | WO 01/55106 | 8/2001 |
| WO | WO 01/55107 | 8/2001 |
| WO | WO 01/55109 | 8/2001 |
| WO | WO 01/70337 | 9/2001 |
| WO | WO 01/70708 | 9/2001 |
| WO | WO 01/74844 | 10/2001 |
| WO | WO 01/85930 | 11/2001 |
| WO | WO 01/90140 | 11/2001 |
| WO | WO 01/91752 | 12/2001 |

OTHER PUBLICATIONS

Wessells, Hunter; et al.; "Sythetic Melanotropic Peptide Initiates Erections in Men with Psychogenic Erectile DysfunctionL Double-Bline, Placebo Controlled Crossover Study," J Urol, vol. 160(2), Aug. 1998: pp. 389-393.

Hruby, Victor; et al.; "Emerging approaches in molecular dsign of receptor-selective peptide ligands: conformation, topographical and dynamic considerations," J Biochem (1990), vol. 268: pp. 249-262.

"Synthetic Peptides. A Users Guide"; ed. Gregory A. Grant; W.H. Freeman & Co., New York; 1992, pp. 11-24.

\* cited by examiner

```
                        SEQUENCE LISTING

<160> NUMBER OF SEQ ID NOS: 4

<210> SEQ ID NO 1
<211> LENGTH: 4
<212> TYPE: PRT
<213> ORGANISM: Artificial
<220> FEATURE:
<223> OTHER INFORMATION: Core sequence of alpha-MSH

<400> SEQUENCE: 1

His Phe Arg Trp
1

<210> SEQ ID NO 2
<211> LENGTH: 4
<212> TYPE: PRT
<213> ORGANISM: Artificial
<220> FEATURE:
<223> OTHER INFORMATION: Synthetic melanocortin-specific metallopeptide
      sequence
<220> FEATURE:
<221> NAME/KEY: MISC_FEATURE
<222> LOCATION: (2)..(2)
<223> OTHER INFORMATION: Xaa is Nal 2'

<400> SEQUENCE: 2

Ala Xaa Cys Trp
1

<210> SEQ ID NO 3
<211> LENGTH: 5
<212> TYPE: PRT
<213> ORGANISM: Artificial
<220> FEATURE:
<223> OTHER INFORMATION: Synthetic melanocortin-specific metallopeptide
      sequence

<400> SEQUENCE: 3

Phe Arg Trp Cys Lys
1               5

<210> SEQ ID NO 4
<211> LENGTH: 5
<212> TYPE: PRT
<213> ORGANISM: Artificial
<220> FEATURE:
<223> OTHER INFORMATION: Synthetic melanocortin-specific metallopeptide
      sequence

<400> SEQUENCE: 4

Phe Arg Trp Cys Trp
1               5
```

MELANOCORTIN METALLOPEPTIDES FOR TREATMENT OF SEXUAL DYSFUNCTION

CROSS-REFERENCE TO RELATED APPLICATIONS

This application is a continuation of PCT/US02/04431, filed Feb. 13, 2002, which claims priority to provisional application 60/268591, filed Feb. 13, 2001.

BACKGROUND OF THE INVENTION

1. Field of the Invention (Technical Field)

The present invention relates to metallopeptides, metal ion-complexed peptidomimetics, and metallo-constructs for the treatment of sexual dysfunction in animals, including both male erectile dysfunction and female sexual dysfunction in humans, including methods and formulations for use and administration.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Melanocortin Receptors. A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, mid-brain and brainstem, and melanocortin-5 receptors (MC5-R), expressed in a wide distribution of peripheral tissues. Peptides specific for melanocortin receptors have been reported to have a wide variety of biological activities.

Significant work has been done in determining the structure of melanocortin receptors, including both the nucleic acid sequences encoding for the receptors and the amino acid sequences constituting the receptors. See, for example, International Patent Applications No. PCT/US98/12098 and PCT/US99/16862 and U.S. Pat. No. 5,994,087. A large number of ligands specific for melanocortin receptors, both agonists and antagonists, have also been developed. See, for example, International Patent Applications No. PCT/US98/03298 (iodo group-containing melanocortin receptor-specific linear peptide), PCT/GB99/01388 (MC1-R specific linear peptides), PCT/GB99/01195 (MC3-R, MC4-R and MC5-R specific cyclic peptides), PCT/US99/04111 (MC1-R specific peptide antagonists for melanoma therapy), PCT/US99/09216 (isoquinoline compounds as melanocortin receptor ligands), PCT/US99/13252 (spiropiperdine derivatives as melanocortin receptor agonists), PCT/US00/14930 (substituted piperidines as melanocortin-4 receptor agonists), PCT/US00/19408 (peptide-based melanocortin receptor-3 ligands to treat sexual dysfunction), and U.S. Pat. No. 6,054,556 (cyclic lactam peptides as MC1-R, MC3-R, MC4-R and MC5-R antagonists). In addition, a large number of patents teach various methods of screening and determining melanocortin receptor-specific compounds, as for example International Patent Applications No. PCT/US97/15565, PCT/US98/12098 and PCT/US99/16862 and U.S. Pat. Nos. 5,932,779 and 5,994,087.

In general, compounds specific for MC1-R are believed to be useful for treatment of melanoma, including use as radiotherapeutic or drug delivery agent, and as diagnostic imaging agents, particularly when labeled with a diagnostic radionuclide. Compounds specific for MC3-R, MC4-R or MC5-R are believed to be useful in regulation of energy homeostasis, including use as agents for attenuating food intake and body weight gain, for treatment of obesity, for use in treatment of anorexia, as a weight gain aid, and other treatment of other food intake and metabolism-related purposes. Compounds specific for MC3-R and MC4-R are believed to be useful as agents for treatment of sexual dysfunction, including male erectile dysfunction. Compounds specific for MC3-R and MC4-R are believed to be useful to regulate blood pressure, heart rate and other neurophysiologic parameters. Other melanocortin receptor peptides are believed to be useful as tanning agents, to increase melanin production, such as peptides that are MC1-R agonists. Compounds specific for MC1-R and MC3-R may be useful in regulation of inflammatory processes.

Sexual Dysfunction and Melanocortin Receptors. Sexual dysfunction, including both penile erectile dysfunction or impotence and female sexual dysfunction, are common medical problems. Significant effort has been devoted over the last twenty or more years to develop methods, devices and compounds for treatment of sexual dysfunction. While more effort has been undertaken for treatment of penile erectile dysfunction, female sexual dysfunction is also an area to which significant research and effort has been devoted.

At present, one commonly used orally administered drug for treatment of sexual dysfunction in the male is Viagra®, a brand of sildenafil, which is a phosphodiesterase 5 inhibitor, increasing the persistence of cyclic guanosine monophosphate and thereby enhancing erectile response. There are several other medical treatment alternatives currently available depending on the nature and cause of the impotence problem. Some men have abnormally low levels of the male hormone testosterone, and treatment with testosterone injections or pills may be beneficial. However, comparatively few impotent men have low testosterone levels. For many forms of erectile dysfunction, treatment may be undertaken with drugs injected directly into the penis, including drugs such as papaverin, prostaglandin $E_1$, phenoxybenzamine or phentolamine. These all work primarily by dilating the arterial blood vessels and decreasing the venous drainage. Urethral inserts, such as with suppositories containing prostaglandin, may also be employed. In addition, a variety of mechanical aids are employed, including constriction devices and penile implants.

A variety of treatments have also been explored for female sexual dysfunction, including use of sildenafil, although the United States Food and Drug Administration has not specifically approved such use. Testosterone propionate has also been employed to increase or augment female libido.

Melanocortin receptor-specific compounds have been explored for use of treatment of sexual dysfunction. In one report, a cyclic α-melanocyte-stimulating hormone ("α-MSH") analog, called Melanotan-II, was evaluated for erectogenic properties for treatment of men with psychogenic erectile dysfunction. Wessells H. et al., *J Urology* 160:389-393 (1998); see also U.S. Pat. No. 5,576,290, issued Nov. 19, 1996 to M. E. Hadley, entitled Compositions and Methods for the Diagnosis and Treatment of Psychogenic Erectile Dysfunction and U.S. Pat. No. 6,051,555, issued Apr. 18, 2000, also to M. E. Hadley, entitled Stimulating Sexual Response in Females. The peptides used in U.S. Pat. Nos. 5,576,290 and 6,051,555 are also described in U.S. Pat. No. 5,674,839, issued Oct. 7, 1997, to V. J. Hruby, M. E. Hadley and F. Al-Obeidi, entitled Cyclic Analogs of Alpha-MSH Fragments, and in U.S. Pat. No. 5,714,576, issued Feb. 3, 1998, to V. J. Hruby, M. E. Hadley and F. Al-Obeidi, entitled Linear Analogs of Alpha-MSH Fragments. Melanotan-II is a peptide of the formula Ac-Nle-cyclo(-Asp-His-D-Phe-Arg-Trp-Lys)-NH$_2$. Additional related peptides are disclosed in U.S. Pat. Nos. 5,576,290, 5,674,839, 5,714,576 and 6,051,555, and commonly owned pending application PCT/US00/18217, entitled Compositions And Methods For Treatment Of Sexual Dysfunction, filed Jun. 29, 2000. The application PCT/US00/18217 discloses a peptide of the formula Ac-Nle-cyclo(-Asp-His-D-Phe-Arg-Trp-Lys)-OH which may be administered by a variety of routes, including nasal administration. These peptides are described as being useful for both the diagnosis and treatment of psychogenic sexual dysfunction in males and females. These peptides are related to the structure of melanocortins.

In use of Melanotan-II, significant erectile responses were observed, with 8 of 10 treated men developing clinically apparent erections, and with a mean duration of tip rigidity greater than 80% for 38 minutes with Melanotan-II compared to 3.0 minutes with a placebo. The drug was administered by subcutaneous abdominal wall injection, at doses ranging from 0.025 to 0.157 mg/kg body weight. Transient side effects were observed, including nausea, stretching and yawning, and decreased appetite.

Other peptides and constructs have been proposed as ligands that alter or regulate the activity of one or more melanocortin receptors. For example, International Patent Application No. PCT/US99/09216, entitled Isoquinoline Compound Melanocortin Receptor Ligands and Methods of Using Same, discloses two compounds that induce penile erections in rats. However, these compounds were administered by injection at doses of 1.8 mg/kg and 3.6 mg/kg, respectively, and at least one compound resulted in observable side effects, including yawning and stretching. Other melanocortin receptor-specific compounds with claimed application for treatment of sexual dysfunction are disclosed in International Patent Application No. PCT/US99/13252, entitled Spiropiperidine Derivatives as Melanocortin Receptor Agonists, and in International Patent Application Nos. PCT/US00/14930 and PCT/US00/19408.

In general, all natural melanocortin peptides share the same active core sequence, His$^6$-Phe$^7$-Arg$^8$-Trp$^9$ (SEQ ID NO:1) of native α-MSH, including melanotropin neuropeptides and adrenocorticotropin. MC3-R has the highest expression in the arcuate nucleus of the hypothalamus, while MC4-R is more widely expressed in the thalamus, hypothalamus and hippocampus. A central nervous system mechanism for melanocortins in the induction of penile erection has been suggested by experiments demonstrating penile erection resulting from central intracerebroventricular administration of melanocortins in rats. While the mechanism of induction of erectile response has not been fully elucidated, it has been generally accepted that the response involves the central nervous system, and binding to MC3-R and/or MC4-R.

Patent Cooperation Treaty Patent Application Serial No. PCT/US00/16396, entitled Melanocortin Receptor-Specific Metallopeptide Constructs, Combinatorial Libraries and Applications, filed on Jun. 14, 2000, commonly owned with this application, teaches melanocortin-specific metallopeptides. Patent Cooperation Treaty Patent Application Serial No. PCT/US99/29743, entitled Metallopeptide Combinatorial Libraries and Applications, filed Dec. 14, 1999, U.S. Pat. No. 6,027,711, entitled Structurally Determined Metallo-Constructs and Applications, issued Feb. 22, 2000, and U.S. Pat. No. 5,891,418, entitled Peptide—Metal Ion Pharmaceutical Constructs and Applications, issued Apr. 6, 1999, all commonly owned with this application, each teach metallopeptides generally. The specifications of the foregoing applications are incorporated herein by reference.

SUMMARY OF THE INVENTION
(DISCLOSURE OF THE INVENTION)

In one embodiment, the invention provides a construct comprising a metal ion-binding domain comprising two or more linked residues forming an $N_3S_1$ ligand complexed to a metal ion, wherein the construct is conformationally constrained in a structure that is an agonist for at least one of MC-3 or MC-4 receptors, and stimulates a sexual and/or erectile response in a mammal.

In the compositions of this invention, the metal ion-binding domain can be complexed with a metal ion, and such compositions are included within the invention. The invention further includes compositions wherein the composition is substantially more specific for MC-3 or MC-4, or both, when the metal ion-binding domain is complexed with a metal ion than is the composition when the metal ion-binding amino acid sequence is not complexed with a metal ion.

The invention further comprises a method for stimulating sexual response in a mammal, comprising administering a pharmaceutically sufficient amount of a composition comprising a peptide or pharmaceutically acceptable salt thereof as described above, wherein the peptide is complexed to a metal ion. In this method, the mammal may be a male or a female. The composition may further comprises a pharmaceutically acceptable carrier. In the method, administering may includee administering by a method of administration such as administration by injection, administration through mucous membranes, buccal administration, oral administration, dermal administration, inhalation administration, nasal administration, parenteral administration, pulmonary administration, ocular administration, sublingual administration and vaginal administration. In the event of nasal administration, it may be nasal administration of a metered amount of a formulation comprising an aqueous buffer.

A primary object of the present invention is a melanocortin receptor-specific pharmaceutical for use in treatment of sexual dysfunction.

A second object is to provide a metallopeptide-based melanocortin receptor-specific pharmaceutical for use in treatment of male sexual dysfunction, including erectile dysfunction.

Another object is to provide a metallopeptide-based melanocortin receptor-specific pharmaceutical for use in treatment of sexual dysfunction which is effective by intravenous administration.

Another object is to provide a metallopeptide-based melanocortin receptor-specific pharmaceutical for use in treatment of sexual dysfunction which is effective by nasal administration.

Another object is to provide a peptide-based melanocortin receptor-specific pharmaceutical for use in treatment of sexual dysfunction with substantially reduced incidence of undesirable side effects.

Another object of this invention is to provide peptide-metal ion complexes specific for melanocortin receptors and which have a higher level of stability and are less susceptible to proteolysis than either the uncomplexed peptide, or other peptides known in the art.

Another object of this invention is to provide peptide-metal ion complexes which are specific for melanocortin receptors MC3-R and/or MC4-R and which are agonists or antagonists.

Another object of this invention is to provide peptides which are not conformationally restricted in the absence of a metal ion, whereby an uncomplexed peptide is either inactive or demonstrates low potency and selectivity for melanocortin receptors, but which is conformationally restricted on complexation with a metal ion and specific for determinable melanocortin receptors with high potency.

Another object of this invention is to utilize metal complexation in a peptide specific for melanocortin receptors to cause specific regional conformational restrictions in the peptide so that the peptide conformation at the metal binding site is conformationally fixed on metal complexation.

Another object of this invention is to complex a peptide to a metal ion, whereby the resulting metallopeptide is specific for melanocortin receptors, and exhibits a preferred in vivo biodistribution profile, rate and mode of clearance, bioavailability and pharmacokinetics in mammals.

Another object of this invention is to provide peptide-metal ion complexes specific for melanocortin receptors that can transit the gut-blood barrier, without significant enzymatic or peptidase degradation, and may be adapted for oral administration.

Other objects, advantages and novel features, and the further scope of applicability of the present invention, will be set forth in part in the detailed description to follow, taken in conjunction with the accompanying drawings, and in part will become apparent to those skilled in the art upon examination of the following, or may be learned by practice of this invention. The objects and advantages of this invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

Figure 1:
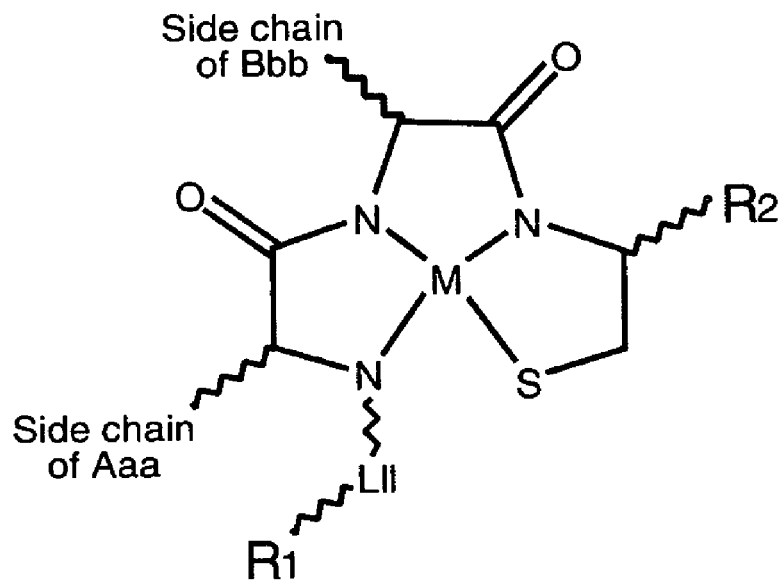
FIG. 1 is a molecular structure for Template 1.

Best Modes for Carrying Out the Invention

Definitions. Certain terms as used throughout the specification and claims are defined as follows:

The terms "bind," "binding," "complex," and "complexing," as used throughout the specification and claims, are generally intended to cover all types of physical and chemical binding, reactions, complexing, attraction, chelating and the like.

The "peptides" of this invention can be a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or f) produced by any other means for producing peptides.

By employing chemical synthesis, a preferred means of production, it is possible to introduce various amino acids which do not naturally occur along the chain, modify the N- or C-terminus, and the like, thereby providing for improved stability and formulation, resistance to protease degradation, and the like.

The term "peptide" as used throughout the specification and claims is intended to include any structure comprised of two or more amino acids, including chemical modifications and derivatives of amino acids. For the most part, the peptides of this invention comprise fewer than 100 amino acids, and preferably fewer than 60 amino acids, and most preferably ranging from 3 to about 20 amino acids. The amino acids forming all or a part of a peptide may be naturally occurring amino acids, stereoisomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

The "amino acids" used in this invention, and the term as used in the specification and claims, include the known naturally occurring protein amino acids, which are referred to by both their common three letter abbreviation and single letter abbreviation. See generally *Synthetic Peptides: A User's Guide*, G A Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference. In addition, the following abbreviations have the meanings giving:

| Abu | gamma-amino butyric acid |
|---|---|
| 2-Abz | 2-amino benzoic acid |
| 3-Abz | 3-amino benzoic acid |
| 4-Abz | 4-amino benzoic acid |
| Achc | 1-amino-cyclohexane-1-carboxylic acid |
| Acpc | 1-amino-cyclopropane-1-carboxylic acid |
| 12-Ado | 12-amino dodecanoic acid |
| 7-Ahept | 7-amino heptanoic acid |
| Aic | 2-aminoindane-2-carboxylic acid |
| 6-Ahx | 6-amino hexanoic acid |
| Amb | 4-(aminomethyl)-benzoic acid |

-continued

| | |
|---|---|
| Amc | 4-(aminomethyl)-cyclohexane carboxylic acid |
| 8-Aoc | 8-amino octanoic acid |
| Arg(Tos) | $N^G$-para-tosyl-arginine |
| Asp(anilino) | beta-anilino-aspartic acid |
| Asp(3-Cl-anilino) | beta-(3-chloro-anilino)-aspartic acid |
| Asp(3,5-diCl-anilino) | beta-(3,5-dichloro anilino)-aspartic acid |
| D/L-Atc | (D,L)-2-aminotetralin-2-carboxylic acid |
| 11-Aun | 11-amino undecanoic acid |
| AVA | 5-amino valeric acid |
| Bip | biphenylalanine |
| Br | bromo |
| Bzl | benzyl |
| Bz | benzoyl |
| Cha | cyclohexylalanine |
| Chg | cyclohexylglycine |
| Dip | 3,3-Diphenylalanine |
| Et- | ethyl |
| GAA | epsilon-guanidino acetic acid |
| GBzA | 4-guanidino benzoic acid |
| B-Gpa | 3-guanidino propionic acid |
| GVA(Cl) | beta-chloro-epsilon-guanidino valeric acid |
| Hphe | homophenylalanine |
| HyP | hydroxy proline |
| Idc | indoline-2-carboxylic acid |
| Igl | indanylglycine |
| Inp | isonipecotic acid |
| Lys(Z) | N-epsilon-benzyloxycarbonyl-lysine |
| Me- | methyl |
| Nal 1' | 3-(1-naphthyl)alanine |
| Nal 2' | 3-(2-naphthyl)alanine |
| (N-Bzl)Nal 2' | N-benzyl-3-(2-naphthyl) alanine |
| (N-PhEt)Nal 2' | N(2-phenylethyl)-3-(2-naphthyl) alanine |
| OcHx | cyclohexyl ester |
| Phg | phenylglycine |
| pF-Phe | para-fluoro-phenylalanine |
| Phe(4'-Br) | 4-bromo-phenylalanine |
| Phe(4'-CF$_3$) | 4-trifluoromethyl-phenylalanine |
| Phe(4'-Cl) | 4-chloro-phenylalanine |
| Phe(2'-Cl) | 2 chloro-phenylalanine |
| Phe(2',4'-diCl) | 2,4,-dichloro-phenylalanine |
| Phe(3',4'-diCl) | 3,4-dichloro-phenylalanine |
| Phe(3',4'-diF) | 3,4-difluoro-phenylalanine |
| Phe(4'-I) | 4-iodo-phenylalanine |
| Phe(3',4'-di-OMe) | 3,4,-dimethoxy-phenylalanine |
| Phe(4'-Me) | 4-methyl-phenylalanine |
| Phe(4'-NO$_2$) | 4-nitro-phenylalanine |
| Pip | pipecolic acid |
| Qal(2') | beta-(2-quinolyl)-alanine |
| Sal | 3-styrylalanine |
| TFA | trifluoroacetyl |
| Tic | 1,2,3,4-tetrahydroisoquinoline-3-carboxylic acid |
| Tiq | 1,2,3,4-tetrahydroisoquinoline-1-carboxytic acid |
| Tle | tert-butylalanine |
| Tpi | 1,2,3,4-tetrahydronorharman-3-carboxylic acid |
| Tyr(Bzl) | O-benzyl-tyrosine |
| Tyr(Bzl diCl 2,6) | O-(2,6 dichloro)benzyl-tyrosine |
| Z | benzyloxycarbonyl |

In the listing of compounds according to the present invention, conventional amino acid residues have their conventional meaning as given in Chapter 2400 of the *Manual of Patent Examining Procedure*, 7$^{th}$ Ed. Thus, "Nle" is norleucine; "Asp" is aspartic acid; "His" is histidine; "D-Phe" is D-phenylaline; "Arg" is arginine; "Trp" is tryptophan; "Lys" is lysine; "Gly" is glycine; "Pro" is proline; "Tyr" is tyrosine, "Ser" is serine and so on.

A single amino acid, including stereoisomers and modifications of naturally occurring protein amino acids, non-protein amino acids, post-translationally modified amino acids, enzymatically synthesized amino acids, derivatized amino acids, constructs or structures designed to mimic amino acids, and the like, including all of the foregoing, is sometimes referred to herein as a "residue."

The peptides of this invention also include a metal ion, which may be an ionic form of any element in metallic form, including but not limited to metals and metalloids. The metal ion may, but need not, be radioactive, paramagnetic or superparamagnetic. The metal ion can be of any oxidation state of any metal, including oxidation states of vanadium (V), manganese (Mn), iron (Fe), cobalt (Co), nickel (Ni), copper (Cu), zinc (Zn), gallium (Ga), arsenic (As), selenium (Se), yttrium (Y), molybdenum (Mo), technetium (Tc), ruthenium (Ru), rhodium (Rh), palladium (Pd), silver (Ag), cadmium (Cd), indium (In), tin (Sn), tungsten (W), rhenium (Re), osmium (Os), iridium (Ir), platinum (Pt), gold (Au), mercury (Hg), thallium (Tl), lead (Pb), bismuth (Bi), polonium (Po), astatine (At), samarium (Sm), europium (Eu), and gadolinium (Gd). The metal ion can also be a radionuclide of any of the foregoing, including In, Au, Ag, Hg, Tc, Re, Sn, At, Y and Cu. A preferred metal ion with a tetradentate coordination sphere is Re. For radiopharmaceutical applications, or applications wherein a radioisotope is desirable for screening, an alpha-, gamma- or beta-emitting radionuclide may be employed.

The coordination sphere of various common metal ions, in general, is tetradentate to hexadentate. In one embodiment according to this invention, an amino acid or amino acid mimetic sequence is included within peptide such that it contains the desired number of groups (4 to 6 in most cases) for complexing with the metal. The molecule is designed so that, upon complexing with a metal, it forms a mimic of a reverse turn structure about the site of metal complexation. A metal with coordination number 4, 5 or 6, and complexing respectively with an amino acid sequence forming a tetra, penta, or hexadentate ligand, will fold and constrain the ligand. The amino acid or amino acid mimetic sequence forming a ligand is defined as the metal ion-binding domain ("MBD") of the peptide or peptidomimetic. A highly flexible molecule like a peptide, in other words, is folded to form a kind of reverse turn upon its complexation with a metal. This resulting turn is a highly constrained structure in the conformational sense.

The biological-binding domain ("BBD") of the peptide or peptidomimetic is defined in the specification and claims as a sequence of one or more amino acids which constitute a biologically active sequence, exhibiting binding to a melanocortin-associated receptor, including MC3-R and MC4-R. The BBD also includes any sequence, which may be consecutive amino acids or mimetics (sychnological) or non-consecutive amino acids or mimetics (rhegnylogical) which forms a melanocortin-associated ligand, which ligand is capable of forming a specific interaction with its acceptor or receptor. The term "receptor" is intended to include both acceptors and receptors. The receptor may be a biological receptor. The sequence or BBD may transmit a signal to the cells, tissues or other materials associated with the biological receptor after binding, but such is not required. The BBD may be either an agonist or antagonist, or a mixed agonist-antagonist. A peptide or peptidomimetic complexed to a metal ion with such a BBD constitutes a member of a "specific binding pair," which specific binding pair is made up of at least two different molecules, where one molecule has an area on the surface or in a cavity which specifically binds to a particular spatial and polar organization of the other molecule. Frequently, the members of a specific binding pair are referred to as ligand and receptor.

The BBD is further defined to include the portion of a construct, wherein the construct is a peptidomimetic, peptide-like, or metallo-construct molecule, which upon binding of the construct with a metal ion, is biologically active, exhibiting binding to a melanocortin receptor found on cells, tissues, organs and other biological materials. The BBD may, in this instance, be sychnological or rhegnylogical, and generally has the attributes and functions of a BBD of a peptide. The BBD may be coextensive with all or a portion of the MBD, so that the same amino acids or other residues which constitute the MBD also constitute all or a part of the BBD. In some instances, one or more amino acids of the MBD will form a part of the BBD, and one or more additional amino acids, which are not part of the MBD, form the remainder of the BBD.

Conformational constraint refers to the stability and preferred conformation of the three-dimensional shape assumed by a peptide or other construct. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure. See generally *Synthetic Peptides: A User's Guide*, cited above.

The primary structure of a peptide is its amino acid sequence. The secondary structure deals with the conformation of the peptide backbone and the folding up of the segments of the peptide into regular structures such as α-helices, β-sheets, turns and the like. Thus, the three-dimensional shape assumed by a peptide is directly related to its secondary structure. See generally *Synthetic Peptides: A User's Guide*, cited above, including the text, figures and tables set forth at pages 24-33, 39-41 and 58-67. A global structure refers to a peptide structure that exhibits a preference for adopting a conformationally constrained three-dimensional shape.

The product resulting from the methods set forth herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

In general, the peptide compounds of this invention may be synthesized by solid-phase synthesis and purified according to methods known in the art. Any of a number of well-known procedures utilizing a variety of resins and reagents may be used to prepare the compounds of this invention.

The peptides of this invention may be in the form of any pharmaceutically acceptable salt. Acid addition salts of the compounds of this invention are prepared in a suitable solvent from the peptide and an excess of an acid, such as hydrochloric, hydrobromic, sulfuric, phosphoric, acetic, trifluoroacetic, citric, tartric, maleic, succinic or methanesulfonic. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

The invention provides a pharmaceutical composition that includes a peptide of this invention and a pharmaceutically acceptable carrier. The carrier may be a liquid formulation, and is preferably a buffered, isotonic, aqueous solution. Pharmaceutically acceptable carriers also include excipients, such as diluents, carriers, lyophilization bulking agents and the like, and additives, such as stabilizing agents, preservatives, solubilizing agents, buffers and the like, as hereafter described.

Routes of Administration. If it is administered by injection, the injection may be intravenous, subcutaneous, intramuscular, intraperitoneal or other means known in the art. The metallopeptides of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the metallopeptides of invention are introduced across an epidermal layer of cells may be employed. Administration means may include administration through mucous membranes, buccal administration, oral administration, dermal administration, inhalation administration, nasal administration and the like. The dosage for treatment of male erectile dysfunction is administration, by any of the foregoing means or any other means known in the art, of an amount sufficient to bring about an erection of the penis in a male. The dosage for treatment of female sexual dysfunction is administration, by any of the foregoing means or any other means known in the art, of an amount sufficient to bring about the desired response.

The metallopeptides of this invention may be formulated or compounded into pharmaceutical compositions that include at least one peptide of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride or sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide of this invention over a period of time.

In general, the actual quantity of metallopeptides of this invention administered to a patient will vary between fairly wide ranges depending upon the mode of administration, the formulation used, and the response desired.

Nasal or Intrapulmonary Administration. By "nasal administration" is meant any form of intranasal administration of any of the metallopeptides of this invention. The metallopeptides may be in an aqueous solution, such as a solution including saline, citrate or other common excipients or preservatives. The metallopeptides may also be in a dry or powder formulation.

In an alternative embodiment, metallopeptides of this invention may be administered directly into the lung. Intrapulmonary administration may be performed by means of a metered dose inhaler, a device allowing self-administration of a metered bolus of a metallopeptide of this invention when actuated by a patient during inspiration.

The metallopeptides of this invention may be formulated with any of a variety of agents that increase effective nasal absorption of drugs, including peptide drugs. These agents should increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, the metallopeptide may be appropriately buffered by means of saline, acetate, phosphate, citrate, tartrate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, tartrate and the like, a 50 mM solution may be employed. In addition to buffering agents, a suitable preservative may be employed, to prevent or limit bacteria and other microbial growth. One such preservative that may be employed is 0.05% benzalkonium chloride.

It is also possible and contemplated that the metallopeptide may be in a dried and particulate form. In a preferred embodiment, the particles are between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 μm. One type of dry powder inhaler in current use is Glaxo's Rotahaler™, which dispenses a unit dose of powder into a tube, and employs patient suction for inhalation of the powder. Other, more advanced and preferred dry powder inhalers have been or are in development, which include propellants and the like.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

In one preferred embodiment, a dry powder inhaler is employed which includes a piezoelectric crystal that deaggregates a dry powder dose, creating a small powder "cloud." Once the powder cloud is generated, an electrostatically charged plated above the powder cloud lifts the drug into the air stream. The user with one relatively easy breath can then inhale the powder. The device may be breath activated, utilizing a flow sensor that activates the electronic components upon the start of inhalation, and thereby eliminating the need for coordination of activation and breathing rhythms by the user.

Synthesis of Peptides. A free thiol (SH) group is preferred for complexation of most metal ions to the peptides of this invention, and in many cases an SH group is necessary in order to form a stable exchange-inert complex with a metal. Peptides with free SH groups, however, are easily oxidized in air and in solution, and can often form a disulfide-linked dimer. If more than one free SH group is present in a molecule, oxidation may lead to a complex polymer. Similarly, if a mixture of different peptides or organic molecules with free SH groups are prepared, oxidation generally leads to a complex mixture of polymers of unknown composition.

A variety of SH protecting groups have been employed for a variety of purposes, including radiopharmaceutical manufacture and formulation. For example, in its protected form S-Benzoylmercaptoacetyl-glycyl-glycyl-glycine (Bz-$MAG_3$) has been used to complex Tc-99m ($^{99m}$Tc) under conditions where the S-Bz group splits during $^{99m}$Tc complexation. The use of S-Bz protection, however, is not compatible with methods of peptide synthesis.

In one embodiment, peptides of this invention which incorporate an SH group employ S-protected derivatives. The SH protecting group is chosen such that (a) the synthesis of peptide derivatives with S-protecting group is compatible with methods of solution and solid phase peptide synthesis, so that the S-protecting group is stable during synthetic procedures, and (b) the S-protecting group can be deprotected in situ, without cleavage from the resin in the case of solid phase synthesis, during the metal complexation step. Many prior art methods, such as Bz-$MAG_3$, meet at most only one of the two criteria specified above (Bz-$MAG_3$ meets only criterion (a) above).

One OSPG meeting the criteria specified above, and which can be used in this invention, employs an $S^tBu$ (S-thio-butyl or S-t-butyl) group to protect the SH group. The $S^tBu$ group is stable under both the acidic and basic conditions typically employed in peptide synthesis. Further, the $S^tBu$ group may be cleaved by reduction using a suitable phosphine reagent, which reduction step may be employed immediately prior to or in conjunction with complexation of a metal ion to the peptide. Such OSPG cleavage does not cleave the peptide from the resin, or otherwise alter the structure of the peptide.

Another OSPG meeting the criteria specified above and suitable for this invention employs an S-Acm (S-acetamidomethyl) group to protect the SH group. The Acm group is also stable under the acid and base conditions usually employed during peptide synthesis. The S-Acm group may be removed by treatment of S-Acm-protected peptide or peptide resin with mercury (II) acetate or silver (I) tertrafluoroborate, which liberates the thiol peptide in its mercury or silver ion-complexed state. Free thiol-containing peptide can then be recovered by treating the mercury or silver ion and thiol complexed salts with an excess of a thiol-containing reagent, such as beta-mercaptoethanol or dithiothreitol. The resulting peptide is then used for metal complexation. Alternatively, the mercury or silver ion and thiol complexed peptide may be directly treated with a metal ion complexing reagent to form the desired metallopeptide.

Other examples of OSPGs for metallopeptides include 4-methoxytrityl (Mmt), 3-nitro-2-pyridinesulfenyl (Npys)

and S-sulfonate (SO$_3$H). Mmt is selectively removed upon treatment with 1% TFA in dichloromethane. Npys and S-sulfonate are selectively removed by treatment with a thiol-containing reagent such as beta-mercaptoethanol or dithiothreitol or a phosphine reagent such as tributyl phosphine. The Npys group (R. G. Simmonds R G et al: *Int J Peptide Protein Res*, 43:363,1994) is compatible with Boc chemistry for peptide synthesis and the S-sulfonate (Maugras I et al: *Int J Peptide Protein Res,* 45:152, 1995) is compatible with both Fmoc and Boc chemistries. Similar OSPGs derived from homologous series of S-alkyl, or S-aryl, or S-aralkyl may also be used in this invention. A primary characterization of the OSPG is that its use results in the formation of a disulfide (S—S) bond utilizing one sulfur atom each from the thiol-containing amino acid and the protecting group. In addition, the resulting disulfide (S—S) bond is cleavable by the use of any of a variety of disulfide cleaving agents, including but not limited to phosphine- and thiol-containing reagents.

The method employing S$^t$Bu protected SH groups, or other OSPGs, may be employed for the synthesis of peptides in either solid phase or solution. For solid phase, peptides may be synthesized by use of conventional Fmoc chemistry. In the case of conventional Fmoc chemistry, Fmoc-L-Cys-(S$^t$Bu) is coupled to an appropriate resin, via one or more intermediate amino acids, and additional amino acids are thereafter coupled to the L-Cys-(S$^t$Bu) residue. S$^t$Bu may be employed with either L- or D-Cys, and any of a variety of other amino acids, including designer or unnatural amino acids and mimics thereof, characterized by an SH group available for binding to a metal ion, including, but not limited to, 3-mercapto phenylananine and other related 3-mercapto amino acids such as 3-mercapto valine (penicillamine); 2-mercaptoacetic acid; 3-mercaptopropionic acid; 2-mercaptopropionic acid; 3-mercapto-3,3,-dimethyl propionic acid; 3-mercapto,3-methyl propionic acid; 3-mercapto-3,3,-diethyl proprionic acid; 2-mercapto,2-methyl acetic acid; 3-cyclopentamethlene,3-mercaptopropionic acid; 2-cyclopentamethlene,2-mercaptoacetic acid and related amino acids. In all these cases, S-protection can be by S$^t$Bu, S-Acm, Mmt, Npys, S-sulfonate and related groups, as described above.

Metal Ion Complexation to MBD. The complexation of metal ions peptides, and specifically to the MBD, is achieved by mixing the peptide with the metal ion. This is conveniently done in solution, with the solution including an appropriate buffer. In one approach, the metal ion is, when mixed with the peptide or peptidomimetic constituents, already in the oxidation state most preferred for complexing to the MBD. Some metal ions are complexed in their most stable oxidation state, such as calcium (II), potassium (I), indium (III), manganese (II), copper (II), zinc (II) and other metals. In other instances, the metal must be reduced to a lower oxidation state in order to be complexed to the MBD. This is true of ferric, stannic, pertechnetate, perrhenate and other similar metal ions. Thus ferric ions are reduced to ferrous ions, stannic to stannous, pertechnetate to technetiumoxo[V], perrhenate to rheniumoxo[V] and so on. Reduction may be performed prior to mixing with the sequences, simultaneously with mixing with the sequences, or subsequent to mixing with the sequences. Any means of reduction of metal ions to the desired oxidation state known to the art may be employed.

For tetradentate coordination with a metal ion, rhenium is a preferred ion. Solid phase resin bound peptide or peptidomimetic sequences may be labeled with rhenium ion by treatment with the rhenium transfer agent ReOCl$_3$(PPh$_3$)$_2$ in the presence of 1,8-Diazabicyclo[5,4,0] undec-7-ene as a base. The sequences may then be cleaved from the resin. Alternatively, peptide sequences in solution may similarly be labeled by treatment with the rhenium transfer agent ReOCl$_3$(PPh$_3$)$_2$ in the presence of 1,8-Diazabicyclo[5,4,0] undec-7-ene as a base. Metal complexation in the presence of 1,8-Diazabicyclo[5,4,0]undec-7-ene (DBU) as a base can conveniently be accomplished at ambient room temperature.

In an alternative method of metal complexation a mild base, such as sodium acetate, can be used. In this case the thiol-containing sequence, either in solution or bound to solid phase, is taken in a suitable solvent, such as DMF, NMP, MeOH, DCM or a mixture thereof, and heated to 60-70° C. with the rhenium transfer agent ReOCl$_3$(PPh$_3$)$_2$ in the presence of sodium acetate for 15 minutes. Similarly, other bases such as triethylamine, ammonium hydroxide and so on, may be employed. According to this invention, MeOH is a preferred choice of solvent for rhenium complexation in the case of S-deprotected peptides in solution. The solvent choice for S-deprotected peptides still attached to the solid phase is guided mainly by considerations of superior solvation (swelling) of the solid phase. DMF and NMP may be employed. Various mixtures of these solvents, also in combination with MeOH, and DCM, CHCl$_3$ and so on, may also be employed to yield optimized complexation results.

In one embodiment of this invention, an S$^t$Bu protected peptide is treated in situ with rhenium transfer agent in the presence of DBU and tributylphosphine to effect S-deprotection and rhenium complexation in one pot. Alternately, complexation of rhenium to the S$^t$Bu protected peptide in the presence of rhenium perrhenate may be accomplished by treatment with Sn[II]Cl$_2$. This reagent effects S-deprotection as well as conversion of ReO$_4$ to ReO in situ to permit complexation of the rhenium to the S-deprotected peptide. A preferred procedure in this invention is the use of S$^t$Bu protected peptide with S-deprotection by treatment with tributylphosphine, and metal complexation of the resulting peptide utilizing ReOCl$_3$(PPh$_3$)$_2$ in the presence of DBU at room temperature.

Structural Diversity of Melanocortin Receptor-Specific Peptides for Treatment of Sexual Dysfunction. Examples of molecular templates that may be employed in this invention are shown below for tetradentate metal ion complexation. In general, these molecular templates define groups of metallopeptides of this invention which, by substitution as provided, give rise to melanocortin receptor-specific compounds, useful for treatment of sexual dysfunction, which may be either agonist or antagonist compounds. The templates are provided without the metal ion, it being understood that the compounds exhibit enhanced specificity for melanocortin receptors only upon metal ion complexation.

R$_1$-Lll-Aaa-Bbb-Ccc-R$_2$                  Template 1 and

R$_1$-Bbb-Aaa-Ccc-R$_2$                      Template 2

Where R$_1$ is any functionality that potentiates the intrinsic activity of the remainder of the molecule, including but not limited to providing an auxiliary or secondary receptor contact. Any of a variety of amino acids and non-peptide groups may be employed, including an amino acid chain from one to about four neutral or charged L- or D-configuration amino acid residues. If R$_1$ is a non-peptide group, it may be a linear or branched alkyl, aryl, alkene, alkenyl or aralkyl chain.

Where Aaa is an L- or D-configuration cationic amino acid with a positively charged side chain. Preferred amino acids include L-configuration Lys, Arg, Orn, Dpr or Dbu, and derivatives, analogs or homologs thereof, including both natural and synthetic amino acids. Aaa provides an N (nitrogen atom) for metal ion complexation.

Where Bbb is an L- or D-configuration amino acid with an aromatic side chain. Preferred amino acids include D-configuration Phe, Phe(4'-Cl), Phe(3',4'-DiCl), Phe(4'-nitro), Phe(4'-Me), Bip, Hphe, Pgl, Trp, Nal 1', Nal 2', Ser(Bzl), Lys(Z), Lys(Z-2'Br), Lys(Bz), Thr(Bzl), Cys(Bzl), or Tyr (BzlCl$_2$), and derivatives, analogs or homologs thereof. The aromatic ring in Bbb may be functionalized with halogen, alkyl or aryl groups. Bbb provides an N for metal ion complexation.

Where Ccc is an amino acid that provides both an N, from the alpha amino group, and an S (sulfur atom), from a side chain group, for metal ion complexation. Preferred amino acids include L- or D-configuration Cys, Pen and Hcys.

Where Lll is a D-configuration amino acid with an aromatic side chain. Preferred amino acids include D-configuration Phe, Phe(4'-Cl), Phe(3',4'-diCl), Phe(4'-NO$_2$), Phe(4'-Me), Bip, Hphe, Pgl, Trp, Nal 1', Nal 2', Ser(Bzl), Lys(Z), Lys(Z-2'Br), Lys(Bz), Thr(Bzl), Cys(Bzl), or Tyr(BzlCl$_2$), and derivatives, analogs or homologs thereof. The aromatic ring in Lll may be functionalized with halogen, alkyl or aryl groups. Lll does not provide an N for metal ion complexation.

Where R$_2$ is an amino acid with an aromatic side chain. Preferred amino acids include L- or D-configuration Phe, Trp, Phe(4'-Cl), Phe(3',4'-diCl), Phe(4'-NO$_2$), Phe(4'-Me), Bip, Hphe, Pgl, Trp, Nal 1', Nal 2', Ser(Bzl), Lys(Z), Lys(Z-2'Br), Lys(Bz), Thr(Bzl), Cys(Bzl) or Tyr(BzlCl$_2$), and derivatives, analogs or homologs thereof, including both natural and synthetic amino acids. The C-terminus may be free or amidated. R$_2$ may also be the corresponding des-carboxyl amino acid of any of the foregoing. Alternatively, R$_2$ may be eliminated.

Figure 2:
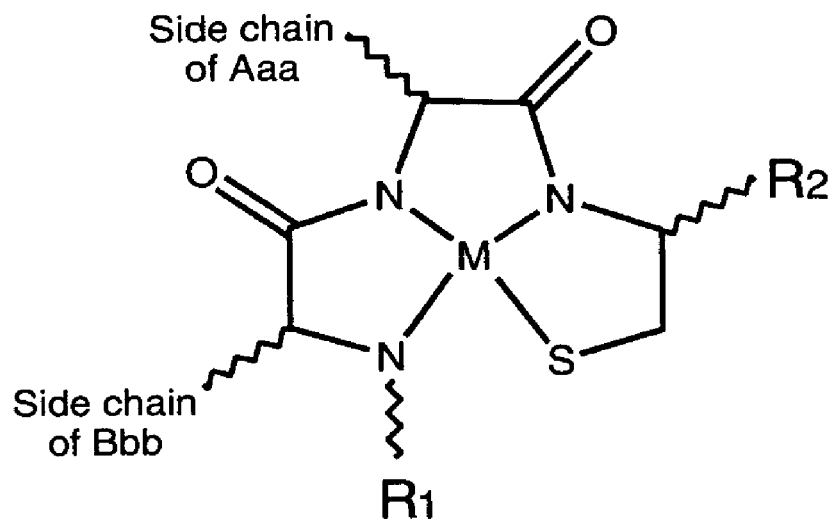
FIG. 2 is a molecular structure for Template 2.

FIG. 1 depicts the structure of Template 1, and FIG. 2 depicts the structure of Template 2, in both cases showing coordination with a tetradenate coordination sphere metal ion, resulting in an N$_3$S$_1$ metal ion bond.

R$_1$-Ddd-Bbb-Aaa-R$_3$   Template 3

Where R$_1$, Bbb and Aaa are as described above.

Where Ddd is an amino acid that provides an S, from a side chain group, for metal ion complexation. Preferred amino acids include L- or D-configuration Cys, Pen and Hcys.

Where R$_3$ is an amino acid with an aromatic side chain that provides an N for metal ion complexation. Preferred amino acids include L- or D-configuration Phe, Trp, Phe(4'-Cl), Phe(3',4'-DiCl), Phe(4'-NO$_2$), Phe(4'-Me), Bip, Hphe, Pgl, Trp, Nal 1', Nal 2', Ser(Bzl), Lys(Z), Lys(Z-2'Br), Lys(Bz), Thr(Bzl), Cys(Bzl) or Tyr(BzlCl$_2$), and derivatives, analogs or homologs thereof, including both natural and synthetic amino acids. The C-terminus may be free or amidated. R$_3$ may also be the corresponding des-carboxyl amino acid of any of the foregoing.

Figure 3:
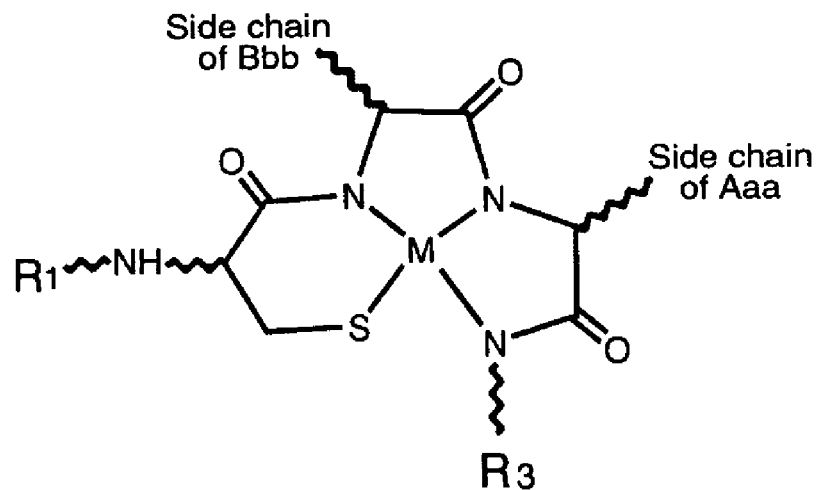
FIG. 3 is a molecular structure for Template 3.

FIG. 3 depicts the structure of Template 3, showing coordination with a tetradenate coordination sphere metal ion, resulting in an N$_3$S$_1$ metal ion bond.

R$_4$-Eee-Bbb-Ccc-R$_2$   Template 4

Where R$_2$, Bbb and Ccc are as described above.
Where R$_4$ is a functionality that provides a cationic center. Preferred amino acids include L- or D-configuration Lys, Arg, Orn, Dpr or Dbu, and derivatives, analogs or homologs thereof, including both natural and synthetic amino acids. The N-terminus of the amino acid may be functionalized with any of a variety of neutral amino acid and non-peptide groups, including linear or branched alkyl, aryl, alkene, alkenyl or aralkyl chains.

Where Eee is an uncharged L- or D-configuration amino acid that provides an N for metal ion complexation. Preferred amino acids include Gly and L-configuration Ala, Nle, Leu, Val, Phe or Trp, and derivatives, analogs or homologs thereof, including both natural and synthetic amino acids. In a preferred embodiment, Eee is an amino acid with an aliphatic side chain.

Figure 4:
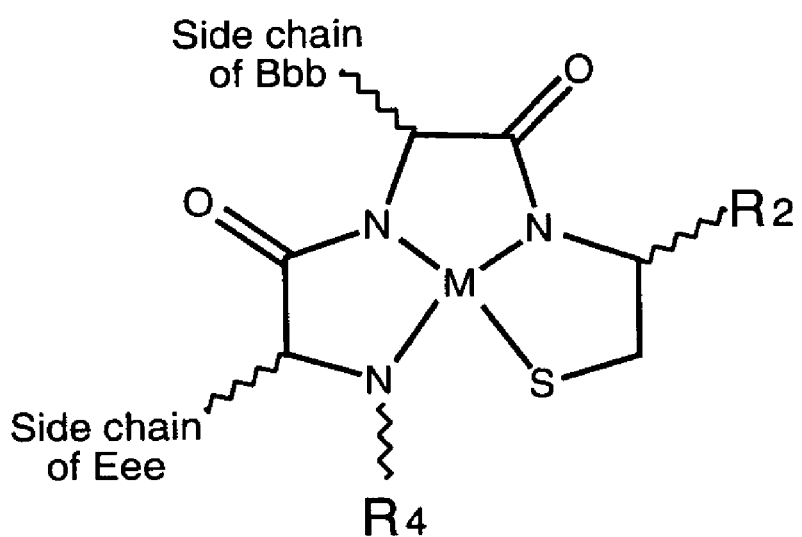
FIG. 4 is a molecular structure for Template 4.

FIG. 4 depicts the structure of Template 4, showing coordination with a tetradenate coordination sphere metal ion, resulting in an N$_3$S$_1$ metal ion bond.

R$_1$-Fff-Aaa-Ggg-Ccc-R$_5$   Template 5

Where R$_1$, Aaa and Ccc are as described above.

Where Fff is an L- or D-configuration aromatic amino acid. Preferred amino acids include D-configuration Phe, Phe (4'-Cl), Phe(3',4'DiCl), Phe(4'-NO$_2$), Phe(4'-Me), Bip, Hphe, Pgl, Trp, Nal 1', Nal 2', Ser(Bzl), Lys(Z), Lys(Z-2'Br), Lys(Bz), Thr(Bzl), Cys(Bzl), Tyr(BzlCl$_2$), Tic, Tiq or Tpi, and derivatives, analogs or homologs thereof, including both natural and synthetic amino acids. The aromatic ring in Fff may be substituted with halogen, alkyl or aryl groups. Fff does not provide an N for metal ion complexation.

Where Ggg is an L- or D-configuration aromatic amino acid. Preferred amino acids include L-configuration Phe, Phe (4'-Cl), Phe(3',4'DiCl), Phe(4'-NO$_2$), Phe(4'-Me), Bip, Hphe, Pgl, Trp, Nal 1', Nal 2', Ser(Bzl), Lys(Z), Lys(Z-2'Br), Lys(Bz), Thr(Bzl), Cys(Bzl) or Tyr(BzlCl$_2$), and derivatives, analogs or homologs thereof, including both natural and synthetic amino acids. The aromatic ring in Ggg may be substituted with halogen, alkyl or aryl groups. Ggg provides an N for metal ion complexation.

Where R$_5$ is preferably an amide, substituted amide, ester or carboxylate group. R$_5$ may also be and L- or D-configuration amino acid or amino acid amide, including an aromatic, aliphatic, neutral or charged amino acid.

Figure 5:
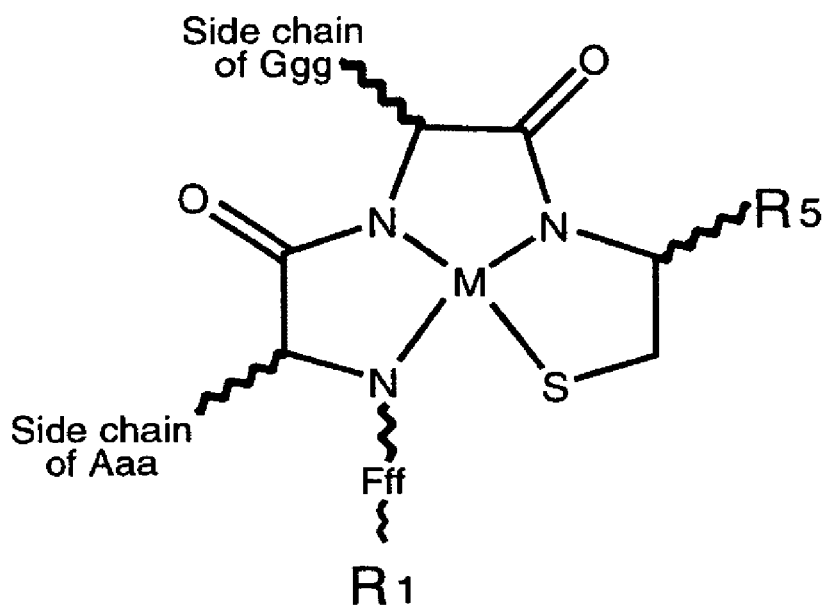
FIG. 5 is a molecular structure for Template 5.

FIG. 5 depicts the structure of Template 5, showing coordination with a tetradenate coordination sphere metal ion, resulting in an N$_3$S$_1$ metal ion bond.

R$_1$-Hhh-Aaa-Bbb-Ccc-R$_5$   Template 6

Where R$_1$, Aaa, Bbb, Ccc and R$_2$ are as described above.

Where Hhh is an L- or D-configuration cationic amino acid with a positively charged side chain. Preferred amino acids include L-configuration Lys, Arg, Orn, Dpr or Dbu, and derivatives, analogs or homologs thereof, including both natural and synthetic amino acids. Hhh does not provide an N for metal ion complexation.

Figure 6:
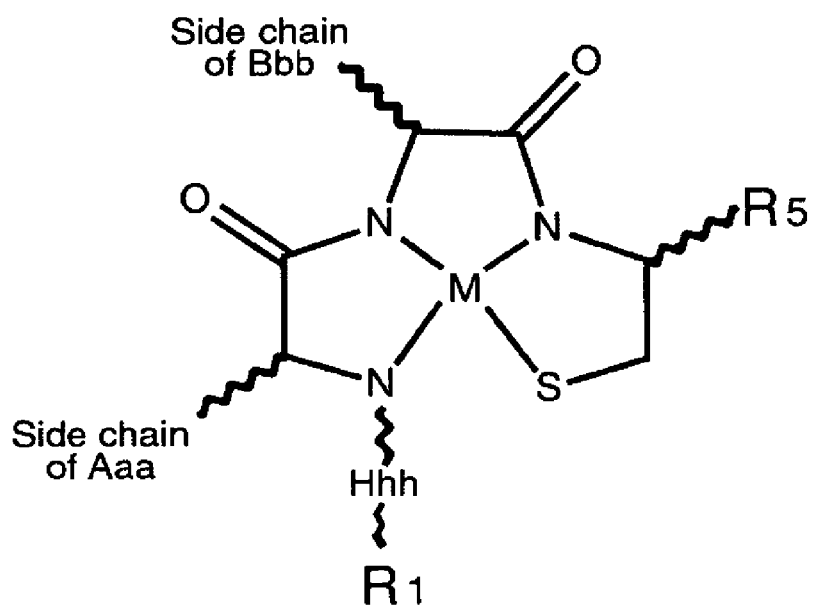
FIG. 6 is a molecular structure for Template 6.

FIG. 6 depicts the structure of Template 6, showing coordination with a tetradenate coordination sphere metal ion, resulting in an N$_3$S$_1$ metal ion bond.

R$_1$-Iii-Iii-Ccc-Jjj-Kkk-R$_2$   Template 7

Where R$_1$, Ccc and R$_2$ are as described above.
Where Iii is an L- or D-configuration amino acid that provides an N for metal ion complexation. Preferred amino acids includes Ala, Gly, Nle, Val. Leu, Ile, His, Lys, or Arg, and derivatives, analogs or homologs thereof, including both natural and synthetic amino acids.

Where Jjj is an L- or D-configuration amino acid with an aromatic side chain. Preferred amino acids include D-configuration Phe, Phe(4'-Cl), Phe(3',4'-DiCl), Phe(4'-NO$_2$), Phe(4'-Me), Bip, Hphe, Pgl, Trp, Nal 1', Nal 2', Ser(Bzl), Lys(Z), Lys(Z-2'Br), Lys(Bz), Thr(Bzl), Cys(Bzl), or Tyr (BzlCl$_2$), and derivatives, analogs or homologs thereof. The aromatic ring in Jjj may be functionalized with halogens, alkyl or aryl groups. Jjj does not provide an N for metal ion complexation.

Where Kkk is an L- or D-configuration cationic amino acid with a positively charged side chain. Preferred amino acids include L-configuration Lys, Arg, Orn, Dpr or Dbu, and derivatives, analogs or homologs thereof, including both natural and synthetic amino acids. Aaa does not provide an N for metal ion complexation.

Figure 7:
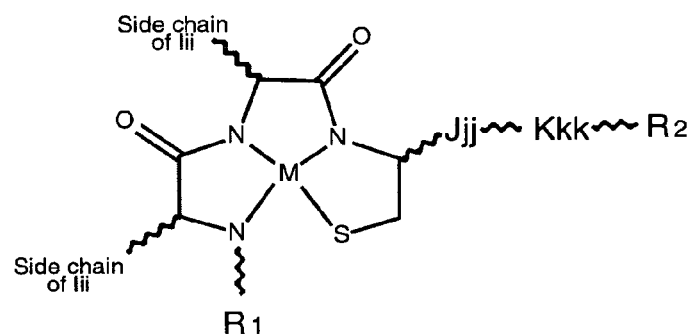
FIG. 7 is a molecular structure for Template 7.

FIG. 7 depicts the structure of Template 7, showing coordination with a tetradenate coordination sphere metal ion, resulting in an N$_3$S$_1$ metal ion bond.

The foregoing templates may be employed with tetradentate coordination sphere metal ions, such as various forms of technetium and rhenium. Corresponding templates may be constructed for use with metal ions of other coordination spheres.

Representative Peptides of this Invention. Representative peptides of this invention include, but are not limited to, the following:

3'-Br Phenyl acetyl-Arg-Arg-D-Phe(4'-Cl)-Cys-Trp-NH$_2$;
Ac-Nle-Ala-His-D-Phe(3'-Cl)-Arg-Trp-Cys-Trp-NH$_2$; and
Heptanoyl-Ser(Bzl)-D-Nal 2'-Arg-D-Trp-Cys-NH$_2$.

Peptides that may be used in treatment of sexual dysfunction, including erectile dysfunction, include the sequences:

Ac-Nle-Ala-His-D-Phe-Arg-Trp-Cys-NH$_2$;
3'-Br Phenyl acetyl-Arg-Arg-D-Phe(4'-Cl)-Cys-Trp-NH$_2$; and
Ac-Nle-Ala-His-D-Phe(3'-Cl)-Arg-Trp-Cys-Trp-NH$_2$ when such peptides are complexed to a metal ion, preferably a rhenium metal ion.

Peptides that may be employed as antagonists, to inhibit the effectiveness of a melanocortin-receptor specific agonist, include the sequences:

D-(N-Bzl)Nal 2'-Arg-Trp-Cys-NH$_2$;
Heptanoyl-Ser(Bzl)-D-Nal 2'-Arg-Trp-Cys-NH$_2$; and
Heptanoyl-Ser(Bzl)-D-Nal 2'-Arg-D-Trp-Cys-NH$_2$ when such peptides are complexed to a metal ion, preferably a rhenium metal ion.

The invention is further illustrated by the following non-limiting examples.

EXAMPLE 1

Competitive Binding Assay

Rhenium-complexed metallopeptides of the formulas given in Table 1 were prepared, with the metallopeptides complexed with rhenium using the rhenium transfer agent ReOCl$_3$(PPh$_3$)$_2$ in the presence of 1,8-Diazabicyclo[5,4,0]undec-7-ene as a base, as disclosed in International Application PCT/US00/16396, filed Jun. 14, 2000, Melanocortin Metallopeptide Constructs, Combinatorial Libraries and Applications, incorporated by reference herein. Affinities of compounds were measured using membranes from HEK-293 cells containing cloned human melanocortin receptor subtypes 3, 4 and 5. MC1-R membranes were isolated from B$_{16}$—F$_{10}$ mouse melanoma cells. The assay tube also contained a chosen concentration of the test peptide of this invention, complexed to a rhenium metal ion as indicated, for determining its efficacy in inhibiting the binding of $^{125}$I-NDP-α-MSH to its receptor. Non-specific binding was measured by complete inhibition of binding of $^{125}$I-NDP-α-MSH in the assay with the presence of 1 µM α-MSH. 100% specific binding was defined as the difference in radioactivity (cpm) bound to cell membranes in the absence and presence of 1 µM α-MSH. The cpm obtained in presence of test compounds were normalized with respect to 100% specific binding to determine the percent inhibition of $^{125}$I-NDP-α-MSH binding.

TABLE 1

Percent Inhibition of $^{125}$I-[Nle$^4$, D-Phe$^7$]-α-MSH Binding by Metallopeptides Specific for Melanotropin Receptors

| Peptide sequence | Conc. [µM] | % Inhibition of Binding | | | |
|---|---|---|---|---|---|
| | | MC1-R | hMC3-R | hMC4-R | hMC5-R |
| Ac-Nle-Ala-His-D-Phe-Arg-Trp-Cys-NH$_2$ | 1 | 91 | 70 | 89 | 93 |
| Ac-Nle-Ala-His-D-Phe-Arg-Cys-Trp-NH$_2$ | 10 | 97 | 14 | 29 | 22 |
| 3'-Br Phenyl acetyl-Arg-Arg-D-Phe(4'-Cl)-Cys-Trp-NH$_2$ | 1 | 97 | NA[1] | 100 | NA[1] |
| Ac-Nle-Ala-His-D-Phe(3'-Cl)-Arg-Trp-Cys-Trp-NH$_2$ | 1 | 101 | NA[1] | 100 | NA[1] |
| D-(N-Bzl)Nal 2'-Arg-Trp-Cys-NH$_2$ | 1 | 34 | 51 | 99 | 95 |
| Heptanoyl-Ser(Bzl)-D-Nal 2'-Arg-Trp-Cys-NH$_2$ | 1 | 19 | 64 | 97 | 98 |
| Heptanoyl-Ser(Bzl)-D-Nal 2'-Arg-D-Trp-Cys-NH$_2$ | 1 | 1 | 6 | 66 | 60 |

[1]Not assayed.

EXAMPLE 2

Functional Activity Assay

Rhenium-complexed metallopeptides were prepared, with functional evaluation of peptides at MC1-R and MC4-R performed by measuring the accumulation of intracellular cAMP in HEK-293 cells expressing MC4-R or B16-F10 mouse melanoma cells expressing MC1-R. Antagonistic activity was determined by measuring the inhibition of α-MSH-induced cAMP levels following exposure to peptide. Cells, suspended in Earle's Balanced Salt Solution containing 10 mM HEPES, pH 7.5, 5 mM MgCl2, 1 mM glutamine, 0.1% albumin and 0.6 mM 3-isobutyl-1-methylxanthine, a phosphodiesterase inhibitor, were plated in 96 well plates at a density of $0.5 \times 10^5$ cells per well. Cells were incubated with the test peptides in the presence or absence of α-MSH for 1 hour at 37° C. cAMP levels were measured by EIA (Amersham) in the cell lysates. Data analysis and $EC_{50}$ values were determined using nonlinear regression analysis with Prism Graph-Pad software. Among compounds of this invention, Ac-Nle-Ala-His-D-Phe-Arg-Cys-Trp-NH$_2$ is a MC1-R specific agonist compound. Ac-Nle-Ala-His-D-Phe-Arg-Trp-Cys-NH$_2$, 3'-Br Phenyl acetyl-Arg-Arg-D-Phe(4'-Cl)-Cys-Trp-NH$_2$ and Ac-Nle-Ala-His-D-Phe(3'-Cl)-Arg-Trp-Cys-Trp-NH$_2$ are MC4-R agonists. D-(N-Bzl)Nal 2'-Arg-Trp-Cys-NH$_2$, Heptanoyl-Ser(Bzl)-D-Nal 2'-Arg-Trp-Cys-NH$_2$, Heptanoyl-Ser(Bzl)-D-Nal 2'-Arg-D-Trp-Cys-NH$_2$ and NH$_2$(CH$_2$)$_6$CO-L-Ser(Bzl)-D-Nal 2'-Arg-D-Trp-Cys-NH$_2$ are MC4-R antagonists. Inhibition binding of NH$_2$(CH$_2$)$_6$CO-L-Ser(Bzl)-D-Nal 2-Arg-D-Trp-Cys-NH$_2$ is given in Table 6.

EXAMPLE 3

Penile Erection Behavior Dose Response Animal Studies

For behavioral experiments test solutions of rhenium-complexed metallopeptides were freshly prepared in DMSO and diluted in saline. Male Sprague-Dawley rats (Taconic) weighing 200-250 g were kept on a 12 hour on/off light cycle with food and water ad libitum. All behavioral studies were performed between 10 a.m. and 5 p.m. Groups of 3-10 rats were treated with the rhenium-complexed metallopeptides at a variety of doses via intravenous (IV) injection. In a second experimental paradigm, rats were treated a selected compound intranasally (IN) using a micropipet to deliver 25 μl of solution into one nostril. Immediately after treatment, rats were placed into individual Lucite cages (27 cm long, 16 cm wide and 25 cm high) for behavioral observation. Rats were observed for 30 minutes and the number of yawns, grooming bouts and penile erections were recorded in three 10-minute bins. Results of IV dosing are shown in Table 2 below.

TABLE 2

| IV Dosing - Penile Erection Behavior in Rats | | |
|---|---|---|
| ReO-Complexed Compound | Dose (μg/kg) | Mean Penile Erections/Rat |
| Ac-Nle-Ala-His-D-Phe-Arg-Trp-Cys-NH$_2$ | 10 | 0.25 |
| Ac-Nle-Ala-His-D-Phe-Arg-Trp-Cys-NH$_2$ | 30 | 0.75 |
| Ac-Nle-Ala-His-D-Phe-Arg-Trp-Cys-NH$_2$ | 50 | 1.0 |
| Ac-Nle-Ala-His-D-Phe-Arg-Cys-Trp-NH$_2$ | 10 | 0 |
| Ac-Nle-Ala-His-D-Phe-Arg-Cys-Trp-NH$_2$ | 50 | 0 |
| 3'-Br Phenyl acetyl-Arg-Arg-D-Phe(4'-Cl)-Cys-Trp-NH$_2$ | 50 | 0.5 |
| Ac-Nle-Ala-His-D-Phe(3'-Cl)-Arg-Trp-Cys-Trp-NH$_2$ | 50 | 0.5 |

TABLE 2-continued

| IV Dosing - Penile Erection Behavior in Rats | | |
|---|---|---|
| ReO-Complexed Compound | Dose (μg/kg) | Mean Penile Erections/Rat |
| D-(N-Bzl)Nal 2'-Arg-Trp-Cys-NH$_2$ | 150 | 0 |
| Heptanoyl-Ser(Bzl)-D-Nal 2'-Arg-Trp-Cys-NH$_2$ | 150 | 0 |
| Heptanoyl-Ser(Bzl)-D-Nal 2'-Arg-D-Trp-Cys-NH$_2$ | 150 | 0 |

Results of intranasal dosing for a selected compound are shown in Table 3 below.

TABLE 3

| IN Dosing - Penile Erection Behavior in Rats | | | | |
|---|---|---|---|---|
| ReO-Complexed Compound | Dose (μg/kg) | Number of Rats | % with Penile Erections | Mean Penile Erections/Rat |
| Ac-Nle-Ala-His-D-Phe-Arg-Trp-Cys-NH$_2$ | 10 | 10 | 70 | 0.9 ± 0.2 |

Vehicle delivered either IV or IN as a control did not induce penile erections (PEs). It is evident from the data that the MC1-R specific ligand, Ac-Nle-Ala-His-D-Phe-Arg-Cys-Trp-NH$_2$, was inactive in inducing PEs in this rat model. Compounds capable of binding to both MC3-R and MC4-R induced a dose-dependent effect in causing PEs. The activity paralleled the receptor binding affinity of the compounds. The data also revealed that the PE activity was induced only by the compounds that behaved as an agonist in the functional cAMP assay. Ac-Nle-Ala-His-D-Phe-Arg-Trp-Cys-NH$_2$ was a of penile erections upon both IV and IN administration. Antagonists, such as D-(N-Bzl)Nal 2'-Arg-Trp-Cys-NH$_2$, Heptanoyl-Ser(Bzl)-D-Nal 2'-Arg-Trp-Cys-NH$_2$, and Heptanoyl-Ser(Bzl)-D-Nal 2'-Arg-D-Trp-Cys-NH$_2$, were inactive in inducing PEs. These results established that agonist metallopeptides capable of binding to MC4-R and/or MC3-R were potent initiators of penile erections in this rat model.

EXAMPLE 4

Combination Penile Erection Behavior Animal Studies

Conditions were as in Example 3 except as noted. Groups of 5-6 rats received an IV dose of either placebo or antagonist 5 minutes prior to an IN dose of either placebo or agonist. Two antagonists were used: ReO[Heptanoyl-Ser(Bzl)-D-Nal 2'-Arg-Trp-Cys-NH$_2$] and SHU9119 (Hruby V J, Lu D, Sharma S D, et al. *J Med Chem* 38:3454-3461 (1995)), Ac-Nle-cyclo(-Asp-His-D-Nal 2'-Arg-Trp-Lys)-NH$_2$. The agonist used was Ac-Nle-cyclo(-Asp-His-D-Phe-Arg-Trp-Lys)-OH. Immediately after IN treatment, rats were placed into individual Lucite cages for observation. Rats were observed for 30 minutes and the number of yawns, grooming bouts and penile erections recorded in three 10-minute bins. Results are shown in Table 4. In combination studies, the antagonist was dosed IV 5 minutes prior to a 50 μg/kg IN dose of Ac-Nle-cyclo(-Asp-His-D-Phe-Arg-Trp-Lys)-OH.

TABLE 4

Combination Studies

| | ReO[Heptanoyl-Ser(Bzl)-D-Nal 2'-Arg-Trp-Cys-NH$_2$]- 200 µg/kg | | | Ac-Nle-cyclo(-Asp-His-D-Nal 2'-Arg-Trp-Lys)-NH$_2$- 5 µg/kg | | |
|---|---|---|---|---|---|---|
| | Number of Rats | Percent with Penile Erections | Mean Penile Erections/ Rat | Number of Rats | Percent with Penile Erections | Mean Penile Erections/ Rat |
| Antagonist | 6 | 0 | 0 | 5 | 0 | 0 |
| Ac-Nle-cyclo(-Asp-His-D-Phe-Arg-Trp-Lys)-OH | 6 | 83 | 1.2 ± 0.3 | 5 | 100 | 1.6 ± 0.2 |
| Combination | 6 | 0 | 0 | 5 | 0 | 0 |

Erectile behavior induced by Ac-Nle-cyclo(-Asp-His-D-Phe-Arg-Trp-Lys)-OH was blocked by either the nonselective MC4-R antagonist, SHU9119, or the selective MC4-R antagonist, ReO[Heptanoyl-Ser(Bzl)-D-Nal 2'-Arg-Trp-Cys-NH$_2$].

EXAMPLE 5

Figure 8:
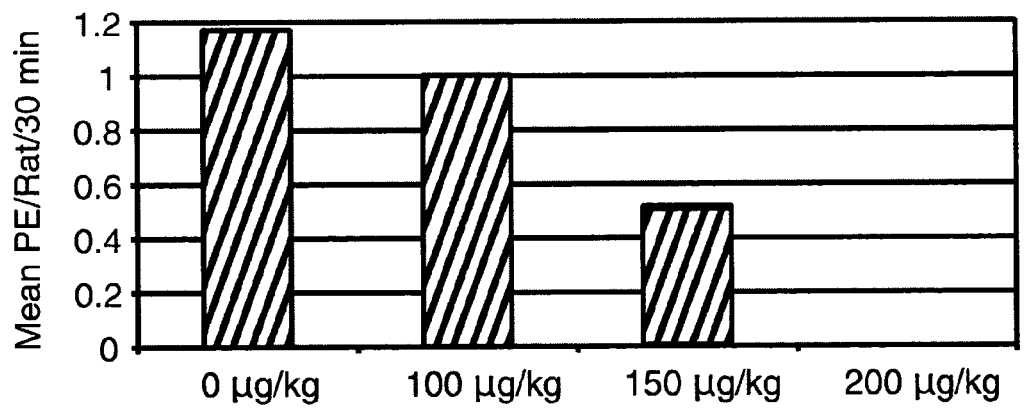
FIG. 8 is a dose response graph of inhibition of erectile response in rats by administration of varying quantities of an MC4-R antagonist prior to administration of an MC4-R agonist with known efficacy for inducing erectile responses.

Inhibition of Penile Erection Caused by a Positive Control Compound by Melanocortin Receptor-Specific Antagonist Metallopeptides These studies were conducted as described above in Example 4 with metallopeptide antagonists administered IV five minutes before IN administration of 50 µg/kg Ac-Nle-cyclo(-Asp-His-D-Phe-Arg-Trp-Lys)-OH. The data is presented in Table 5. The data showed that metallopeptide antagonists were effective in inhibiting the PE response elicited by the potent agonist compound Ac-Nle-cyclo(-Asp-His-D-Phe-Arg-Trp-Lys)-OH in a dose dependent manner. The potency of these antagonists also correlated with their relative binding affinities in the in vitro binding assays. The data presented in Table 5 suggests dose-dependent inhibitory effects of the antagonist test compounds. The inhibitory effect of ReO[Heptanoyl-Ser(Bzl)-D-Nal 2'-Arg-Trp-Cys-NH$_2$] increased with dose; results for IV administration of 0, 100, 150 and 200 µg/kg are plotted in FIG. 8.

TABLE 5

Percent PE Inhibition By Metallopeptide Antagonists Of The Effect Induced By 50 mg/Kg Of Intranasally Administered Ac-Nle-cyclo(-Asp-His-D-Phe-Arg-Trp-Lys)-OH

| | Dose (IV) | | | |
|---|---|---|---|---|
| Antagonist Compound | 100 µg/kg | 150 µg/kg | 200 µg/kg | 500 µg/kg |
| D-(N-Bzl)Nal 2-Arg-Trp-Cys-NH$_2$[2] | 14.28% | 100% | NA[1] | NA[1] |
| Heptanoyl-Ser(Bzl)-D-Nal 2'-Arg-Trp-Cys-NH$_2$[2] | 14.28% | 50% | 100% | NA[1] |
| Heptanoyl-Ser(Bzl)-D-Nal 2'-Arg-D-Trp-Cys-NH$_2$[2] | NA[1] | NA[1] | 50% | 40% |

[1]Not assayed.
[2]Rhenium complexed as in Example 1.

EXAMPLE 6

Competitive Binding Assay of Additional Compounds

Peptide sequences set forth in Table 6 were prepared using conventional synthetic means. The resulting sequences were rhenium-complexed to form metallopeptides, with the metallopeptides complexed with rhenium using the rhenium transfer agent ReOCl$_3$(PPh$_3$)$_2$ in the presence of 1,8-Diazabicyclo[5,4,0] undec-7-ene as a base. Percent inhibition was determined as in Example 1 using the Re-complexed metallopeptides, using the same methods as described therein. All measures are means of triplicate determinations.

Table 6

Percent Inhibition of $^{125}$I-[Nle$^4$, D-Ph $^7$]-α-MSH Binding by Metallopeptides Specific for Melanotropin Receptors

| | Conc. | % Inhibition of Binding | | | |
|---|---|---|---|---|---|
| Peptide Sequence | [µM] | MC1-R | hMC2-R | hMC4-R | hMC5-R |
| 3'-Br Phenyl acetyl-Lys-Ala-D-Phe(2'-Cl)-Cys-Trp-NH$_2$ | 1 | 9 | 19 | 34 | 44 |
| 3'-Br Phenyl acetyl-Lys-Ala-D-Phe(4'-CF$_3$)-Cys-Trp-NH$_2$ | 1 | 10 | 77 | 74 | 83 |
| 3'-Br Phenyl acetyl-Arg-Arg-D-Phe(4'-Me)-Cys-Trp-NH$_2$ | 1 | 85 | 86 | 82 | 94 |
| 3'-Br Phenyl acetyl-Arg-Arg-D-Phe(4'-Me)-Cys-NH$_2$ | 1 | 84 | 87 | 93 | 88 |

Table 6-continued

Percent Inhibition of $^{125}$I-[Nle$^4$, D-Ph$^7$]-α-MSH Binding by Metallopeptides Specific for Melanotropin Receptors

| Peptide Sequence | Conc. [μM] | MC1-R | hMC2-R | hMC4-R | hMC5-R |
|---|---|---|---|---|---|
| 3'-Br Phenyl acetyl-Arg-Arg-D-Phe(3'-Cl)-Cys-Trp-NH$_2$ | 1 | 79 | | 96 | |
| 3'-Br Phenyl acetyl-Arg-Ala-D-Phe(3'-Cl)-Cys-Trp-NH$_2$ | 1 | 23 | | 84 | |
| 3'-Br Phenyl acetyl-Arg-Ala-D-Phe(4'-Me)-Cys-Trp-NH$_2$ | 1 | 25 | | 96 | |
| 3'-Br Phenyl acetyl-Lys-Ala-D-Phe(4'-CF$_3$)-Cys-Trp-NH$_2$ | 1 | 4 | | 96 | |
| 3'-Br Phenyl acetyl-Arg-Arg-D-Phe(4'-Me)-Cys-Trp-NH$_2$ | 1 | 93 | | 98 | |
| 3'-Br Phenyl acetyl-Arg-Arg-D-Phe(4'-Me)-Cys-NH$_2$ | 1 | 94 | | 99 | |
| (R)-4-amino-5-phenyl pentanoyl-Lys-Ala-D-Phe(4'-Me)-Cys-Trp-NH$_2$ | 1 | 23 | | 46 | |
| Heptanoyl-Ser(Bzl)-D-Phe(4'-Br)-Arg-Trp-Cys-NH$_2$ | 0.1 | 21 | | 90 | |
| Heptanoyl-Hphe-D-Phe(4'-Cl)-Arg-Trp-Cys-NH$_2$ | 0.1 | 45 | | 80 | |
| Heptanoyl-Ser(Bzl)-D-Phe(4'-Cl)-Arg-Phe-Cys-NH$_2$ | 0.1 | 11 | | 32 | |
| Heptanoyl-Ser(Bzl)-D-Phe(4'-Cl)-Arg-Tyr-Cys-NH$_2$ | 0.1 | 6 | | 13 | |
| Heptanoyl-Ser(Bzl)-D-Phe(4'-Cl)-Arg-Nal 1'-Cys-NH$_2$ | 0.1 | 3 | | 47 | |
| Heptanoyl-Ser(Bzl)-D-Phe(4'-Cl)-Arg-Nal 2'-Cys-NH$_2$ | 0.1 | 16 | | 94 | |
| Heptanoyl-Ser(Bzl)-D-Phe(4'-Cl)-Arg-Tyr(3'-l)-Cys-NH$_2$ | 0.1 | 12 | | 92 | |
| Heptanoyl-Ser(Bzl)-D-Phe(4'-Cl)-Arg-Phe(2'-Cl)-Cys-NH$_2$ | 0.1 | 9 | | 28 | |
| Heptanoyl-Ser(Bzl)-D-Phe(4'-Cl)-Arg-Phe(3'-Cl)-Cys-NH$_2$ | 0.1 | 27 | | 67 | |
| Heptanoyl-Ser(Bzl)-D-Phe(4'-Cl)-Arg-Tyr(3',5'-Di-l)-Cys-NH$_2$ | 0.1 | 10 | | 85 | |
| Heptanoyl-Ser(Bzl)-D-Phe(4'-Cl)-Arg-Phe(2'-F)-Cys-NH$_2$ | 0.1 | 14 | | 46 | |
| Heptanoyl-Ser(Bzl)-D-Phe(4'-Cl)-Arg-Phe(3'-F)-Cys-NH$_2$ | 0.1 | 19 | | 43 | |
| Heptanoyl-Ser(Bzl)-D-Phe(4'-Cl)-Arg-Asp(OcHx)-Cys-NH$_2$ | 0.1 | 15 | | 25 | |
| D-Phe(2'-Cl)-Lys-Nal 2'-Cys-NH$_2$ | 1 | 51 | | 69 | |
| D-(N-Bzl) Phe(2'-Cl)-Lys-Nal 2'-Cys-NH$_2$ | 1 | 69 | | 97 | |
| 3'-Cl Phenyl acetyl-Arg-Ala-D-Phe(4'-CF$_3$)-Cys-Trp-NH$_2$ | 1 | 21 | | 95 | |
| 3'-Br Phenyl acetyl-Arg-Ala-D-Phe(4'-CF$_3$)-Cys-Trp-NH$_2$ | 1 | 22 | | 95 | |
| 3'-Cl Phenyl acetyl-Arg-Arg-D-Phe(4'-CF$_3$)-Cys-Trp-NH$_2$ | 1 | 85 | | 99 | |
| 3'-Br Phenyl acetyl-Arg-Arg-D-Phe(4'-CF$_3$)-Cys-Trp-NH$_2$ | 1 | 72 | 94 | 89 | 99 |
| Heptanoyl-Ser(Bzl)-D-Phe(2'-Cl)-Lys-Phg-Cys-NH$_2$ | 1 | 16 | | 15 | |
| Heptanoyl-Ser(Bzl)-D-Phe(2'-Cl)-Lys-Phe-Cys-NH$_2$ | 1 | 20 | | 19 | |
| Heptanoyl-Ser(Bzl)-D-Phe(2'-Cl)-Lys-Hphe-Cys-NH$_2$ | 1 | 12 | | 6 | |
| 1'-Naphthyl acetyl-Arg-Arg-D-Phe(4'-Cl)-Cys-Trp-NH$_2$ | 1 | 97 | | 98 | |
| 2'-Naphthyl acetyl-Arg-Arg-D-Phe(4'-Cl)-Cys-Trp-NH$_2$ | 1 | 93 | | 96 | |
| 1'-Naphthyl acetyl-Arg-Arg-D-Phe(3'-Cl)-Cys-Trp-NH$_2$ | 1 | 77 | | 92 | |
| 2'-Naphthyl acetyl-Arg-Arg-D-Phe(3'-Cl)-Cys-Trp-NH$_2$ | 1 | 78 | | 90 | |
| 3'-Br Phenyl acetyl-Arg-Arg-D-Phe(4'-Cl)-Cys-Nal 1'-NH$_2$ | 1 | 90 | 85 | 84 | 89 |
| 3'-Br Phenyl acetyl-Arg-Arg-D-Phe(4'-Cl)-Cys-Nal 2'-NH$_2$ | 1 | 90 | 95 | 96 | 97 |
| 3'-Br Phenyl acetyl-Arg-Arg-D-Phe(3'-Cl)-Cys-Nal 1'-NH$_2$ | 1 | 61 | 49 | 62 | 83 |
| 3'-Br Phenyl acetyl-Arg-Arg-D-Phe(3'-Cl)-Cys-Nal 2'-NH$_2$ | 1 | 65 | 68 | 75 | 89 |
| Hept-Ser(Bzl)-D-Phe(4'-Cl)-Arg-D-Trp-Cys-NH$_2$ | 1 | 24 | 37 | 62 | 79 |
| Heptanoyl-Ala-Nal 2'-Cys-Trp-NH$_2$ (SEQ ID NO: 2) | 1 | 15 | | 18 | |
| Heptanoyl-Ser(Bzl)-D-Phe(4'-Cl)-Arg-Hphe-Cys-NH$_2$ | 1 | 38 | | 43 | |
| Heptanoyl-Ser(Bzl)-D-Phe(4'-Cl)-Arg-Cys(Bzl)-Cys-NH$_2$ | 1 | 30 | | 72 | |
| Heptanoyl-Ser(Bzl)-D-Phe(4'-Cl)-Arg-Tyr(Bzl)-Cys-NH$_2$ | 1 | 16 | | 85 | |
| Heptanoyl-Ser(Bzl)-D-Phe(4'-Cl)-Arg-Nal 2'-Cys-Lys-NH$_2$ | 0.1 | 78 | | 97 | |
| Heptanoyl-Ser(Bzl)-D-Phe(2'-Br)-Lys-Nal 2'-Cys-NH$_2$ | 1 | 27 | | 82 | |
| Heptanoyl-Ser(Bzl)-D-Phe(2'-F)-Lys-Nal 2'-Cys-NH$_2$ | 1 | 57 | | 83 | |
| Ser(Bzl)-D-Phe(2'-Cl)-Lys-Nal 2'-Cys-NH$_2$ | 1 | 33 | | 50 | |
| Heptanoyl-D-Hphe(2'-Cl)-Lys-Nal 2'-Cys-NH$_2$ | 1 | 10 | | 20 | |
| (N-PhEt)-D-Phe(2'-Cl)-Lys-Nal 2'-Cys-NH$_2$ | 0.1 | 64 | | 80 | |
| Ph(CH$_2$)$_3$-CO-D-Phe(2'-Cl)-Lys-Nal 2'-Cys-NH$_2$ | 1 | 17 | | 33 | |
| Ph(CH$_2$)$_2$-CO-D-Phe(2'-Cl)-Lys-Nal 2'-Cys-NH$_2$ | 1 | 0 | | 26 | |
| Ph(CH$_2$)-CO-D-Phe(2'-Cl)-Lys-Nal 2'-Cys-NH$_2$ | 1 | 11 | | 22 | |
| PhCO-D-Phe(2'-Cl)-Lys-Nal 2'-Cys-NH$_2$ | 1 | 60 | | 41 | |
| 3'-Br-Phenylacetyl-Arg-Arg-D-Phe(4'-CH$_2$PO$_3$Et$_3$)-Cys-Trp-NH$_2$ | 1 | 97 | | 61 | |
| 3'-Cl-Phenylacetyl-Arg-Arg-D-Phe(4'-CH$_2$PO$_3$Et$_3$)-Cys-Trp-NH$_2$ | 1 | 97 | | 52 | |
| Heptanoyl-Arg-D-Phe-Gly-Trp-Cys-Lys-NH$_2$ | 1 | 92 | | 32 | |
| Heptanoyl-Ser(Bzl)-D-Nal 2'-Gly-Trp-Cys-Lys-NH$_2$ | 1 | 27 | | 0 | |
| Ac-Nle-Arg-Ala-D-Nal 2'-Cys-Lys-NH$_2$ | 1 | 23 | | 36 | |
| Ac-Nle-Arg-Arg-D-Nal 2'-Cys-Lys-NH$_2$ | 1 | 100 | | 96 | |
| Ser(Bzl)-D-Phe(4'-Cl)-Arg-Nal 2'-Cys-Lys-NH$_2$ | 0.1 | 33 | | 95 | |
| D-Phe(4'-Cl)-Arg-Nal 2'-Cys-Lys-NH$_2$ | 0.01 | 43 | | 73 | |
| Heptanoyl-Ser(Bzl)-D-Phe(4'-Cl)-Gly-Nal 2'-Cys-Lys-NH$_2$ | 1 | 46 | | 5 | |
| Ac-Lys-Ala-D-Phe-D-Cys-Arg-NH$_2$ | 1 | 8 | | 0 | |
| Ac-Nle-Ala-D-Phe-D-Cys-Arg-NH$_2$ | 1 | 22 | | 0 | |
| Ac-Trp-Ala-D-Phe-D-Cys-Arg-NH$_2$ | 1 | 24 | | 0 | |
| Heptanoyl-Ser(Bzl)-D-Phe(4'-Cl)-Arg-Tyr(2',6'-diCl-Bzl)-Cys-NH$_2$ | 1 | 19 | | 0 | |
| Heptanoyl-Ser(Bzl)-D-Nal 2'-Arg-Nal 2'-Cys-NH$_2$ | 1 | 28 | 41 | 91 | 97 |
| Heptanoyl-Ser(Bzl)-D-Phe(4'-Cl)-Arg-Thr(Bzl)-Cys-NH$_2$ | 1 | 4 | | 92 | |
| Heptanoyl-Ser(Bzl)-D-Nal 2'-Arg-Trp-Cys-Lys-NH$_2$ | 1 | 72 | | 100 | |
| Heptanoyl-His-D-Phe-Arg-Trp-Cys-Lys-NH$_2$ | 1 | 100 | | 98 | |
| Heptanoyl-Pro-D-Phe-Arg-Trp-Cys-Lys-NH$_2$ | 1 | 99 | | 97 | |
| Heptanoyl-D-Pro-D-Phe-Arg-Trp-Cys-Lys-NH$_2$ | 1 | 88 | | 71 | |
| Heptanoyl-D-Phe-Arg-Trp-Cys-Lys-NH$_2$ | 1 | 82 | | 75 | |

Table 6-continued

Percent Inhibition of $^{125}$I-[Nle$^4$, D-Ph $^7$]-α-MSH Binding by Metallopeptides Specific for Melanotropin Receptors

| Peptide Sequence | Conc. [μM] | % Inhibition of Binding | | | |
|---|---|---|---|---|---|
| | | MC1-R | hMC2-R | hMC4-R | hMC5-R |
| D-Phe-Arg-Trp-Cys-Lys-NH$_2$ | 1 | 96 | | 81 | |
| Phe-Arg-Trp-Cys-Lys-NH$_2$ (SEQ ID NO: 3) | 1 | 53 | | 64 | |
| Phe-Arg-Trp-Cys-Trp-NH$_2$ (SEQ ID NO: 4) | 1 | 32 | | 24 | |
| D-Phe-Arg-D-Trp-Cys-Trp-NH$_2$ | 1 | 37 | | 32 | |
| Phe-Arg-D-Trp-Cys-Lys-NH$_2$ | 1 | 21 | | 12 | |
| D-Phe-Arg-D-Trp-Cys-Lys-NH$_2$ | 1 | 66 | | 55 | |
| Phe-Arg-D-Trp-Cys-Trp-NH$_2$ | 1 | 37 | | 34 | |
| D-Phe-Arg-Trp-D-Cys-Lys-NH$_2$ | 1 | 23 | | 42 | |
| Ac-Nle-Ala-His-D-Phe-Arg-Trp-D-Cys-Lys-NH$_2$ | 1 | 87 | | 41 | |
| Ac-Lys-Ala-D-Phe-D-Cys-Arg-Trp-NH$_2$ | 1 | 25 | | 13 | |
| Ac-Nle-Ala-D-Phe-D-Cys-Arg-Trp-NH$_2$ | 1 | 29 | | 3 | |
| Ac-Trp-Ala-D-Phe-D-Cys-Arg-Trp-NH$_2$ | 1 | 15 | | 3 | |
| Heptanoyl-Ser(Bzl)-D-Phe(2'-Cl)-Lys-Nal 2'-Cys-NH$_2$ | 1 | 62 | | 91 | |
| D-Phe-Arg-Trp-Cys-Trp-NH$_2$ | 1 | 90 | | 70 | |
| 3'-Br-Phenylacetyl-Lys-Lys-D-Phe(4'-CH$_3$)Cys-Lys-NH$_2$ | 1 | 65 | | 69 | |
| 3'-Br-Phenylacetyl-Lys-Ala-D-Phe(4'-CH$_3$)Cys-Lys-NH$_2$ | 1 | 34 | | 73 | |
| Ac-Nle-Arg-Arg-D-Nal 2'-Cys-Trp-Lys-NH$_2$ | 0.1 | 95 | | 96 | |
| 4'-Aminomethyl-Phenylacetyl Arg-Arg-Ala-D-Phe(4'-Cl)-Cys-Trp-NH$_2$ | 1 | 61 | | 84 | |
| 4'-Aminomethyl-Phenylacetyl-Arg-Arg-D-Phe(4'-Cl)-Cys-Trp-NH$_2$ | 0.1 | 81 | | 57 | |
| D-Phe-Arg-Trp-D-Cys-Trp-NH$_2$ | 1 | 53 | | 45 | |
| 1-Naphthylacetyl-Arg-Arg-D-Phe(4'-Cl)-Cys-Nal 2'-NH$_2$ | 1 | 96 | | 98 | |
| NH$_2$-(CH$_2$)$_6$-CO-Ser(Bzl)-D-Phe(4'-Cl)-Arg-Trp-Cys-NH$_2$ | 0.1 | 28 | | 68 | |
| Ac-Ser(Bzl)-D-Phe(4'-Cl)-Arg-Nal 2'-Cys-NH$_2$ | 1 | 49 | | 97 | |
| Ser(Bzl)-D-Phe(4'-Cl)-Arg-Nal 2'-Cys-NH$_2$ | 1 | 35 | | 99 | |
| NH$_2$-(CH$_2$)$_6$-CO-Ser(Bzl)-D-Nal 2'-Arg-Nal 2'-Cys-NH$_2$ | 1 | 22 | 70 | 95 | 100 |
| Ser(Bzl)-D-Nal 2'-Arg-Nal 2'-Cys-NH$_2$ | 1 | 18 | 23 | 71 | 91 |
| Ser(Bzl)-D-Phe(4'-Cl)-Arg-D-Trp-Cys-NH$_2$ | 1 | 65 | | 82 | |
| NH$_2$-(CH$_2$)$_6$-CO-Ser(Bzl)-D-Phe(4'-Cl)-Arg-D-Trp-Cys-NH$_2$ | 1 | 48 | | 97 | |
| HyP(Bzl)-D-Phe(2'-Cl)-Nal 2'-Cys-NH$_2$ | 1 | 57 | | 85 | |
| Ac-His-HyP(Bzl)-D-Phe(2'-Cl)-Arg-Nal 2'-Cys-NH$_2$ | 1 | 84 | | 99 | |
| 3'-Br Phenyl acetyl-Arg-Arg-D-Bip-Cys-Trp-NH$_2$ | 1 | 91 | 83 | 77 | 99 |
| Ac-Nle-Ala-His-D-Bip-Arg-Cys-Trp-NH$_2$ | 1 | 72 | 100 | | |
| Ac-Nle-Ala-His-D-Bip-Arg-Cys-Bip-NH$_2$ | 1 | 77 | 100 | | |
| 3'-Br Phenyl acetyl-Arg-Arg-D-Bip-Cys-Bip-NH$_2$ | 1 | 56 | 46 | 68 | 92 |
| 3'-Br Phenyl acetyl-Arg-Arg-D-Phe(4'-Cl)-Cys-Bip-NH$_2$ | 1 | 69 | 60 | 78 | 86 |
| Ac-Nle-Ala-His-D-Bip-Arg-Trp-Cys-NH$_2$ | 1 | 99 | 100 | | |
| Heptanoyl-Ser(Bzl)-D-Bip-Arg-Trp-Cys-NH$_2$ | 1 | 84 | 0 | | |
| Ac-Nle-Ala-His-D-Phe-Arg-Bip-Cys-NH$_2$ | 1 | 35 | 100 | | |
| Heptanoyl-Ser(Bzl)-D-Phe(4'-Cl)-Arg-Bip-Cys-NH$_2$ | 1 | 65 | 5 | | |
| Heptanoyl-Ser(Bzl)-D-Bip-Arg-Bip-Cys-NH$_2$ | 1 | 30 | 0 | | |
| Ac-Nle-Ala-His-D-Bip-Arg-Bip-Cys-NH$_2$ | 1 | 95 | 100 | | |
| Ac-Nle-Ala-His-D-Phe-Arg-Cys-Bip-NH$_2$ | 1 | 82 | 100 | | |
| NH$_2$-(CH$_2$)$_6$-CO-Ser(Bzl)-D-Phe(4'-Cl)-Arg-Trp-Cys-NH$_2$ | 1 | 74 | 90 | 94 | 100 |
| 3'-Br-Phenylacetyl-His-Gly-D-Phe(4'-Cl)Trp-Cys-NH$_2$ | 1 | 33 | 14 | 2 | 16 |
| 3'-Br-Phenylacetyl-His-D-Phe(4'-Cl)-Trp-Cys-NH$_2$ | 1 | 41 | 15 | 3 | 40 |
| Ac-Ala-Ala-His-D-Phe-Arg-Cys-Trp-NH$_2$ | 1 | 76 | 0 | 4 | 17 |
| Ac-Ala-His-D-Phe-Arg-Cys-Trp-NH$_2$ | 1 | 61 | 0 | 0 | 9 |
| Ac-Nle-His-D-Phe-Arg-Cys-Trp-NH$_2$ | 1 | 77 | 0 | 2 | 28 |
| Ac-Leu-His-D-Phe-Arg-Cys-Trp-NH$_2$ | 1 | 75 | 0 | 0 | 31 |
| 3'-Phenylpropionyl-His-D-Phe-Arg-Cys-Trp-NH$_2$ | 1 | 75 | 2 | 16 | 50 |
| 3'-(4'-Hydroxyphenyl)propionyl-HiS-D-Phe-Arg-Cys-Trp-NH$_2$ | 1 | 76 | 0 | 0 | 21 |
| 3'-Phenylpropionyl-D-Phe-Arg-Cys-Trp-NH$_2$ | 1 | 3 | 0 | 0 | 44 |
| 3'-(4'-Hydroxyphenyl)propionyl-D-Phe-Arg-Cys-Trp-NH$_2$ | 1 | 7 | 0 | 0 | 14 |
| Naphthlyl-2-acetyl-D-Phe-Arg-Cys-Trp-NH$_2$ | 1 | 7 | 0 | 0 | 56 |
| 4'-Biphenylacetyl-D-Phe-Arg-Cys-Trp-NH$_2$ | 1 | 1 | 0 | 0 | 50 |
| Ac-Nle-Ala-Leu-D-Phe-Arg-Cys-Trp-NH$_2$ | 1 | 81 | 4 | 18 | 87 |
| Ac-Nle-Ala-Phe-D-Phe-Arg-Cys-Trp-NH$_2$ | 1 | 58 | 0 | 16 | 71 |
| Ac-Nle-Ala-Trp-D-Phe-Arg-Cys-Trp-NH$_2$ | 1 | 45 | 0 | 9 | 62 |
| Tic-D-Phe(4'-Cl)-Arg-Trp-Cys-NH$_2$ | 1 | 45 | 71 | 88 | 90 |
| Tic-D-Phe(4'-Cl)-Arg-Cys-NH$_2$ | 1 | 0 | 0 | 3 | 42 |
| Tic-D-Phe(4'-Cl)-Gln-Cys-NH$_2$ | 1 | 2 | 3 | 0 | 13 |
| Tic-D-Phe(4'-Cl)-His-Cys-NH$_2$ | 1 | 15 | 0 | 0 | 37 |
| Tic-D-Phe(4'-Cl)-Lys-Cys-NH$_2$ | 1 | 16 | 0 | 6 | 84 |
| Ac-Nle-Ala-Tyr-D-Phe-Arg-Cys-Trp-NH$_2$ | 1 | 66 | 0 | 0 | 44 |
| Hept-Ser(Bzl)-D-Phe(4'-Cl)-Arg-Trp-Cys-NH$_2$ | 1 | 85 | 85 | 88 | 100 |
| NH$_2$(CH$_2$)$_6$CO-Ser(Bzl)-D-Phe(4'-Cl)-Arg-Trp-Cys-NH$_2$ | 1 | 74 | 87 | 94 | 100 |
| NH$_2$(CH$_2$)$_6$CO-Ser(Bzl)-D-Nal 2'-Arg-Trp-Cys-NH$_2$ | 1 | 14 | 69 | 96 | 95 |
| NH$_2$(CH$_2$)$_6$CO-Ser(Bzl)-D-Nal 2'-Arg-D-Trp-Cys-NH$_2$ | 1 | 6 | 58 | 92 | 83 |
| Hept-Ser(Bzl)-D-Nal 2'-Arg-Nal 2'-Cys-NH$_2$ | 1 | 25 | 62 | 92 | 98 |
| Tic-D-Phe(2'-Cl)-Arg-Trp-Cys-NH$_2$ | 1 | 15 | 26 | 69 | 59 |
| Tic-D-Phe(3'-Cl)-Arg-Trp-Cys-NH$_2$ | 1 | 18 | 41 | 62 | 76 |
| Tic-D-Phe-Arg-Trp-Cys-NH$_2$ | 1 | 14 | 25 | 64 | 69 |

Table 6-continued

Percent Inhibition of $^{125}$I-[Nle$^4$, D-Ph $^7$]-α-MSH Binding by Metallopeptides Specific for Melanotropin Receptors

| Peptide Sequence | Conc. [μM] | % Inhibition of Binding | | | |
|---|---|---|---|---|---|
| | | MC1-R | hMC2-R | hMC4-R | hMC5-R |
| Tic-D-Nal-2'-Arg-Trp-Cys-NH$_2$ | 1 | 10 | 52 | 92 | 83 |
| Ac-Nle-Ala-D-Tyr-D-Phe-Arg-Cys-Trp-NH$_2$ | 1 | 15 | 0 | 1 | 0 |
| Ac-Nle-Ala-Thr-D-Phe-Arg-Cys-Trp-NH$_2$ | 1 | 30 | 8 | 11 | 7 |
| Ac-Nle-Ala-Glu-D-Phe-Arg-Cys-Trp-NH$_2$ | 1 | 0 | 3 | 12 | 0 |
| Ac-Nle-Ala-Arg-D-Phe-Arg-Cys-Trp-NH$_2$ | 1 | 92 | 26 | 39 | 59 |
| Ac-Nle-Ala-Ala-D-Phe-Arg-Cys-Trp-NH$_2$ | 1 | 34 | 9 | 12 | 20 |
| Amc-D-Phe-Arg-Cys-Trp-NH$_2$ | 1 | 7 | 0 | 4 | 8 |
| D-Pro-D-Phe-Arg-Cys-Trp-NH$_2$ | 1 | 53 | 0 | 13 | 67 |
| Idc-D-Phe-Arg-Cys-Trp-NH$_2$ | 1 | 0 | 0 | 4 | 19 |
| Pro-D-Phe-Arg-Cys-Trp-NH$_2$ | 1 | 27 | 0 | 2 | 33 |
| D-Tiq-D-Phe-Arg-Trp-Cys-NH$_2$ | 1 | 5 | 0 | 34 | 23 |
| Tiq-D-Phe-Arg-Trp-Cys-NH$_2$ | 1 | 7 | 7 | 8 | 55 |
| 1-amino-1-cyclohexane carboxyl-D-Phe-Arg-Trp-Cys-NH$_2$ | 1 | 11 | 0 | 1 | 16 |
| 1-amino-1-cyclopentane carboxyl-D-Phe-Arg-Trp-Cys-NH$_2$ | 1 | 23 | 7 | 0 | 14 |
| Aic-D-Phe-Arg-Trp-Cys-NH$_2$ | 1 | 9 | 4 | 18 | 38 |
| Nal 1'-D-Phe-Arg-Trp-Cys-NH$_2$ | 1 | 11 | 3 | 15 | 68 |
| D-Nal 1'-D-Phe-Arg-Trp-Cys-NH$_2$ | 1 | 3 | 0 | 13 | 43 |
| Nal 2'-D-Phe-Arg-Trp-Cys-NH$_2$ | 1 | 8 | 0 | 20 | 62 |
| D-Nal 2'-D-Phe-Arg-Trp-Cys-NH$_2$ | 1 | 11 | 0 | 5 | 13 |
| D-Pro-D-Phe-Arg-Cys-Trp-NH$_2$ | 1 | 1 | 0 | 18 | 35 |
| Nal 1'-D-Phe-Arg-Cys-Trp-NH$_2$ | 1 | 0 | 6 | 12 | 45 |
| Ac-Ala-Ala-Ala-D-Phe-Arg-Cys-Trp-NH$_2$ | 1 | 5 | 0 | 3 | 0 |
| Amb-D-Phe-Arg-Cys-Trp-NH$_2$ | 1 | 39 | 0 | 0 | 1 |
| D-Nal 1'-D-Phe-Arg-Cys-Trp-NH$_2$ | 1 | 22 | 0 | 8 | 48 |
| D-Igl-D-Phe-Arg-Cys-Trp-NH$_2$ | 1 | 49 | 12 | 15 | 39 |
| D-Tiq-D-Phe-Arg-Cys-Trp-NH$_2$ | 1 | 43 | 3 | 13 | 39 |
| Nal 2'-D-Phe-Arg-Cys-Trp-NH$_2$ | 1 | 39 | 13 | 21 | 63 |
| D-Dip-D-Phe-Arg-Cys-Trp-NH$_2$ | 1 | 58 | 8 | 2 | 53 |
| allo-Thr-D-Phe-Arg-Cys-Trp-NH$_2$ | 1 | 66 | 5 | 0 | 31 |
| D-Nal 2'-D-Phe-Arg-Cys-Trp-NH$_2$ | 1 | 50 | 7 | 0 | 52 |
| Igl-D-Phe-Arg-Cys-Trp-NH$_2$ | 1 | 38 | 7 | 14 | 67 |
| Igl-D-Phe-Arg-Cys-Trp-NH$_2$ | 1 | 36 | 0 | 20 | 64 |
| Tiq-D-Phe-Arg-Cys-Trp-NH$_2$ | 1 | 53 | 3 | 16 | 56 |
| Aic-D-Phe-Arg-Cys-Trp-NH$_2$ | 1 | 59 | 0 | 21 | 71 |
| 1-amino-1-cyclohexane carboxyl-D-Phe-Arg-Cys-Trp-NH$_2$ | 1 | 92 | 0 | 14 | 65 |
| 1-amino-1-cyclopentane carboxyl-D-Phe-Arg-Cys-Trp-NH$_2$ | 1 | 78 | 0 | 16 | 60 |
| Bip-D-Phe-Arg-Trp-Cys-NH$_2$ | 1 | 0 | 0 | 19 | 51 |
| 4-Amc-D-Phe-Arg-Trp-Cys-NH$_2$ | 1 | 51 | 0 | 6 | 6 |
| Idc-D-Phe-Arg-Trp-Cys-NH$_2$ | 1 | 12 | 0 | 11 | 0 |
| Amb-D-Phe-Arg-Trp-Cys-NH$_2$ | 1 | 39 | 0 | 0 | 5 |
| Pro-D-Phe-Arg-Trp-Cys-NH$_2$ | 1 | 39 | 0 | 14 | 0 |
| D-Igl-D-Phe-Arg-Trp-Cys-NH$_2$ | 1 | 2 | 0 | 8 | 63 |
| Igl-D-Phe-Arg-Trp-Cys-NH$_2$ | 1 | 70 | 0 | 62 | 36 |
| Z-D-Pyr-D-Phe-Arg-Trp-Cys-NH$_2$ | 1 | 44 | 16 | 46 | 28 |
| D-Dip-D-Phe-Arg-Trp-Cys-NH$_2$ | 1 | 23 | 0 | 34 | 8 |
| Allo-Thr-D-Phe-Arg-Trp-Cys-NH$_2$ | 1 | 28 | 0 | 22 | 2 |
| D-Igl-D-Nal 2'-Arg-Cys-NH$_2$ | 1 | 0 | 1 | 8 | 41 |
| 7-amino-haptanoyl-D-Igl-D-Phe-Arg-Cys-NH$_2$ | 1 | 8 | 0 | 10 | 32 |
| 7-amino-haptanoyl-Ser(Bzl)-D-Nal 2'-Arg-Cys-NH$_2$ | 1 | 3 | 0 | 6 | 34 |
| 7-amino-Heptanoyl-D-Igl-D-Phe-Arg-Trp-Cys-NH$_2$ | 1 | 47 | 0 | 5 | 35 |
| D-Igl-D-Nal 2'-Arg-Trp-Cys-NH$_2$ | 1 | 27 | 73 | 97 | 85 |
| Ser(Bzl)-D-Phe-Arg-Trp-Cys-NH$_2$ | 1 | 27 | 0 | 28 | 69 |
| 3'-Bromo phenyl acetyl-Arg-His-D-Phe(4'-Cl)-Cys-NH$_2$ | 1 | 47 | 11 | 15 | 0 |
| 3'-Bromo phenyl acetyl-Arg-Ala-D-Phe(4'-Cl)-Cys-NH$_2$ | 1 | 90 | 47 | 59 | 15 |
| 3'-Bromo phenyl acetyl-Arg-Trp-D-Phe(4'-Cl)-Cys-NH$_2$ | 1 | 5 | 0 | 17 | 21 |
| 3'-Bromo phenyl acetyl-Arg-Thr-D-Phe(4'-Cl)-Cys-NH$_2$ | 1 | 8 | 6 | 1 | 2 |
| 3'-Bromo phenyl acetyl-Arg-Thr(Bzl)-D-Phe(4'-Cl)-Cys-NH$_2$ | 1 | 16 | 5 | 6 | 21 |
| 3'-Bromo phenyl acetyl-Arg-Ala-D-Phe(4'-Cl)-Cys-Trp-NH$_2$ | 1 | 8 | 35 | 80 | 86 |
| 3'-Bromo phenyl acetyl-Lys-Ala-D-Phe(4'-Me)-Cys-Trp-NH$_2$ | 1 | 0 | 19 | 73 | 80 |
| 3'-Bromo phenyl acetyl-Lys-Ala-D-Phe(3'-Cl)-Cys-Trp-NH$_2$ | 1 | 4 | 13 | 38 | 60 |
| 3'-Bromo phenyl acetyl-Arg-Arg-D-Phe(4'-Cl)-Cys-Trp-NH$_2$ | 1 | 91 | 48 | 92 | 89 |
| 3'-Bromo phenyl acetyl-Arg-Arg-D-Phe(4'-Cl)-Cys-Nal 2'-NH$_2$ | 1 | 79 | 55 | 94 | 93 |
| Ac-Nle-Ala-His-D-Phe-Arg-Nal 2'-Cys-NH$_2$ | 1 | 99 | 40 | 89 | 83 |
| Ac-Nle-Ala-His-D-Phe-Arg-D-Nal 2'-Cys-NH$_2$ | 1 | 100 | 0 | 90 | 54 |
| Ac-Nle-Ala-His-D-Phe-Arg-Nal 1'-Cys-NH$_2$ | 1 | 95 | 22 | 65 | 82 |
| Ac-Nle-Ala-His-D-Phe-Arg-D-Nal 1'-Cys-NH$_2$ | 1 | 93 | 3 | 47 | 5 |
| Ac-Nle-Ala-His-D-Phe-Arg-His-Cys-NH$_2$ | 1 | 58 | 0 | 1 | 0 |
| Ac-Nle-Ala-His-D-Phe-Arg-D-His-Cys-NH$_2$ | 1 | 52 | 0 | 16 | 0 |

Each of the foregoing is merely illustrative, and other equivalent embodiments are possible and contemplated.

Although this invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above are hereby incorporated by reference.

The preceding examples can be repeated with similar success by substituting the generically or specifically described reactants and/or operating conditions of this invention for those used in the preceding examples.

What is claimed is:

1. A manufactured peptide or a pharmaceutically acceptable salt thereof with a metal ion-binding domain consisting of three contiguous amino acids forming an $N_3S_1$ ligand and complexed to a metal ion and a determined biological-function domain, wherein the metal on-complexed peptide or salt thereof is an agonist increasing cAMP production in a functional cAMP assay and specific for at least one of melanocortin receptors MC-3 or MC-4, wherein at least a portion of said biological-function domain is co-extensive with at least a portion of said metal ion-binding domain, and wherein said biological-function domain is conformationally constrained upon complexing said metal ion-binding domain with a metal ion, the peptide being of any of the formulas:

$R_1$-Lll-Aaa-Bbb-Ccc-$R_2$, $R_1$-Bbb-Aaa-Ccc-$R_2$, $R_1$-Ddd-Bbb-Aaa-$R_3$, $R_4$-Eee-Bbb-Ccc-$R_2$, $R_1$-Fff-Aaa-Ggg-Ccc-$R_5$, $R_1$-Hhh-Aaa-Bbb-Ccc-$R_5$, or $R_1$-Iii-Iii-Ccc-Jjj-Kkk-$R_2$, wherein
  $R_1$ is any functionality that potentiates the intrinsic activity of the remainder of the molecule, including but not limited to providing an auxiliary or secondary receptor contact; including any of a variety of amino acids and non-peptide groups, including an amino acid chain from one to about four neutral or charged L- or D-configuration amino acid residues, and further wherein if $R_1$ is a non-peptide group, it comprises a linear or branched alkyl, aryl, alkene, alkenyl or aralkyl chain;
  Aaa is an L- or D-configuration cationic amino acid with a positively charged side chain, including L-configuration Lys, Arg, Orn, Dpr or Dbu, and derivatives, analogs or homologs thereof, including both natural and synthetic amino acids, and further wherein Aaa provides an N (nitrogen atom) for metal ion complexation;
  Bbb is an L- or D-configuration amino acid with an aromatic side chain, including D-configuration Phe, Phe(4'-Cl), Phe(3',4'-di-Cl), Phe(4'-NO₂), Phe(4'-Me), Bip, Hphe, Pgl, Trp, Nal 1', Nal 2', Ser(Bzl), Lys(Z), Lys(Z-2'Br), Lys(Bz), Thr(Bzl), Cys(Bzl), or Tyr(BzlCl₂), and derivatives, analogs or homologs thereof, wherein the aromatic ring in Bbb is optionally functionalized with halogen, alkyl or aryl groups, and further wherein Bbb provides an N for metal ion complexation;
  Ccc is an amino acid that provides both an N, from the alpha amino group, and an S (sulfur atom), from a side chain group, for metal ion complexation, including L- or D-configuration Cys, Pen and Hcys;
  Lll is a D-configuration amino acid with an aromatic side chain, including D-configuration Phe, Phe(4'-Cl), Phe (3',4'-diCl), Phe(4'-NO₂), Phe(4'-Me), Bip, Hphe, Pgl, Trp, Nal 1', Nal 2', Ser(Bzl), Lys(Z), Lys(Z-2'Br), Lys(Bz), Thr(Bzl), Cys(Bzl), or Tyr(BzlCl₂), and derivatives, analogs or homologs thereof, wherein the aromatic ring in Lll is optionally functionalized with halogen, alkyl or aryl groups, and further wherein Lll does not provide an N for metal ion complexation;
  $R_2$ is an amino acid with an aromatic side chain, including L- or D-configuration Phe, Trp, Phe(4'-Cl), Phe(3',4'-diCl), Phe(4'-NO₂), Phe(4'-Me), Bip, Hphe, Pgl, Trp, Nal 1', Nal 2', Ser(Bzl), Lys(Z), Lys(Z-2'Br), Lys(Bz), Thr(Bzl), Cys(Bzl) or Tyr(BzlCl₂), and derivatives, analogs or homologs thereof, including both natural and synthetic amino acids, wherein the C-terminus may optionally be free or amidated, or a corresponding des-carboxyl amino acid of any of the foregoing, or alternatively, $R_2$ may be eliminated;
  Ddd is an amino acid that provides an S, from a side chain group, for metal ion complexation, including L- or D-configuration Cys, Pen and Hcys;
  $R_3$ is an amino acid with an aromatic side chain that provides an N for metal ion complexation, including L- or D-configuration Phe, Trp, Phe(4'-Cl), Phe(3',4'-diCl), Phe(4'-NO₂), Phe(4'-Me), Bip, Hphe, Pgl, Trp, Nal 1', Nal 2', Ser(Bzl), Lys(Z), Lys(Z-2'Br), Lys(Bz), Thr(Bzl), Cys(Bzl) or Tyr(BzlCl₂), and derivatives, analogs or homologs thereof, including both natural and synthetic amino acids, wherein the C-terminus may optionally be free or amidated, or alternatively the corresponding des-carboxyl amino acid of any of the foregoing;
  $R_4$ is a functionality that provides a cationic center, including L- or D-configuration Lys, Arg, Orn, Dpr or Dbu, and derivatives, analogs or homologs thereof, including both natural and synthetic amino acids, wherein the N-terminus of the amino acid may optionally be functionalized with neutral amino acid or non-peptide groups, including linear or branched alkyl, aryl, alkene, alkenyl or aralkyl chains;
  Eee is an uncharged L- or D-configuration amino acid that provides an N for metal ion complexation, including Gly and L-configuration Ala, Nle, Leu, Val, Phe or Trp, and derivatives, analogs or homologs thereof, including both natural and synthetic amino acids, and wherein Eee is optionally an amino acid with an aliphatic side chain;
  Fff is an L- or D-configuration aromatic amino acid, including D-configuration Phe, Phe(4'-Cl), Phe(3',4'-diCl), Phe(4'-NO₂), Phe(4'-Me), Bip, Hphe, Pgl, Trp, Nal 1', Nal 2', Ser(Bzl), Lys(Z), Lys(Z-2'Br), Lys(Bz), Thr(Bzl), Cys(Bzl), Tyr(BzlCl₂), Tic, Tiq or Tpi, and derivatives, analogs or homologs thereof, including both natural and synthetic amino acids, and wherein the aromatic ring in Fff may be substituted with halogen, alkyl or aryl groups, and further wherein Fff does not provide an N for metal ion complexation;
  Ggg is an L- or D-configuration aromatic amino acid, including L-configuration Phe, Phe(4'-Cl), Phe(3',4'-diCl), Phe(4'-NO₂), Phe(4'-Me), Bip, Hphe, Pgl, Trp, Nal 1', Nal 2', Ser(Bzl), Lys(Z), Lys(Z-2'Br), Lys(Bz), Thr(Bzl), Cys(Bzl) or Tyr(BzlCl₂), and derivatives, analogs or homologs thereof, including both natural and synthetic amino acids, and wherein the aromatic ring in Ggg may be substituted with halogen, alkyl or aryl groups, and further wherein Ggg provides an N for metal ion complexation;
  $R_5$ is preferably an amide, substituted amide, ester or carboxylate group, and optionally an L- or D-configuration amino acid or amino acid amide, including an aromatic, aliphatic, neutral or charged amino acid;
  Hhh is an L- or D-configuration cationic amino acid with a positively charged side chain, including L-configuration Lys, Arg, Orn, Dpr or Dbu, and derivatives, analogs or homologs thereof, including both natural and synthetic amino acids, wherein Hhh does not provide an N for metal ion complexation;
  Iii is an L- or D-configuration amino acid that provides an N for metal ion complexation, including Ala, Gly, Nle, Val, Leu, Ile, His, Lys, or Arg, and derivatives, analogs or homologs thereof, including both natural and synthetic amino acids;

Jjj is an L- or D-configuration amino acid with an aromatic side chain, including D-configuration Phe, Phe (4'-Cl), Phe(3',4'-diCl), Phe(4'-NO$_2$), Phe(4'-Me), Bip, Hphe, Pgl, Trp, Nal 1', Nal 2', Ser(Bzl), Lys(Z), Lys (Z-2'Br), Lys(Bz), Thr(Bzl), Cys(Bzl), or Tyr(BzlCl$_2$), and derivatives, analogs or homologs thereof, wherein the aromatic ring in Jjj may be functionalized with halogens, alkyl or aryl groups, and further wherein Jjj does not provide an N for metal ion complexation; and Kkk is an L- or D-configuration cationic amino acid with a positively charged side chain, including L-configuration Lys, Arg, Orn, Dpr or Dbu, and derivatives, analogs or homologs thereof, including both natural and synthetic amino acids, wherein Aaa does not provide an N for metal ion complexation.

2. A peptide comprising 3'-Br Phenyl acetyl-Arg-Arg-D-Phe(4'-Cl)-Cys-Trp-NH$_2$.

3. A peptide comprising Ac-Nle-Ala-His-D-Phe(3'-Cl)-Arg-Trp-Cys-Trp-NH$_2$.

4. A peptide comprising Heptanoyl-Ser(Bzl)-D-Nal 2'-Arg-D-Trp-Cys-NH$_2$.

5. The peptides of claim 2, 3, or 4 wherein said peptide is complexed with a metal ion.

6. A pharmaceutical composition for the treatment of erectile dysfunction in a male mammal comprising a peptide selected from the group consisting of:

Ac-Nle-Ala-His-D-Phe-Arg-Trp-Cys-NH$_2$;
3'-Br Phenyl acetyl-Arg-Arg-D-Phe(4'-Cl)-Cys-Trp-NH$_2$; and
Ac-Nle-Ala-His-D-Phe(3'-Cl)-Arg-Trp-Cys-Trp-NH$_2$ complexed to a metal and a pharmaceutically acceptable carrier.

7. The manufactured peptide or pharmaceutically acceptable salt thereof of claim 1, wherein said composition is substantially more specific for one or both MC-3 and MC-4 melanocortin receptors when said metal ion-binding domain is complexed with said metal ion than is the composition when said metal ion-binding amino acid sequence is not complexed with said metal ion.

8. A method of stimulating erectile response in a male mammal, comprising administering a to the mammal a pharmaceutically sufficient amount of a composition comprising a peptide or peptide salt as in claim 1, wherein the peptide is complexed to a metal ion.

9. The method of claim 8 comprising a method of administration selected from the group consisting of intravenous, subcutaneous, intramuscular, parenteral, intranasal, oral, dermal, inhalation, buccal, pulmonary, ocular, and sublingual administration.

10. A metallopeptide comprising a metal ion complexed to a peptide sequence selected from the group consisting of:

3'-Br Phenyl acetyl-Lys-Ala-D-Phe(2'-Cl)-Cys-Trp-NH$_2$
3'-Br Phenyl acetyl-Lys-Ala-D-Phe(4'-CF$_3$)-Cys-Trp-NH$_2$;
3'-Br Phenyl acetyl-Arg-Arg-D-Phe(4'-Me)-Cys-Trp-NH$_2$;
3'-Br Phenyl acetyl-Arg-Arg-D-Phe(4'-Me)-Cys-NH$_2$;
3'-Br Phenyl acetyl-Arg-Arg-D-Phe(3'-Cl)-Cys-Trp-NH$_2$;
3'-Br Phenyl acetyl-Arg-Arg-D-Phe-Ala-D-Phe(3'-Cl)-Cys-Trp-NH$_2$;
3'-Br Phenyl acetyl-Arg-Ala-D-Phe(4'-Me)-Cys-Trp-NH$_2$;
3'-Br Phenyl acetyl-Lys-Ala-D-Phe(4'-CF$_3$)-Cys-Trp-NH$_2$;
3'-Br Phenyl acetyl-Arg-Arg-D-Phe(4'-Me)-Cys-Trp-NH$_2$;
3'-Br Phenyl acetyl-Arg-Arg-D-Phe(4'-Me)-Cys-NH$_2$;
(R)-4-amino-5-phenyl pentanoyl-Lys-Ala-D-Phe(4'-Me)-Cys-Trp-NH$_2$;
Heptanoyl-Ser(Bzl)-D-Phe(4'-Br)-Arg-Trp-Cys-NH$_2$;
Heptanoyl-Hphe-D-Phe(4'-Cl)-Arg-Trp-Cys-NH$_2$;
Heptanoyl-Ser(Bzl)-D-Phe(4'-Cl)-Arg-Phe-Cys-NH$_2$;
Heptanoyl-Ser(Bzl)-D-Phe(4'-Cl)-Arg-Tyr-Cys-NH$_2$;
Heptanoyl-Ser(Bzl)-D-Phe(4'-Cl)-Arg-Nal 1'-Cys-NH$_2$;
Heptanoyl-Ser(Bzl)-D-Phe(4'-Cl)-Arg-Nal 2'-Cys-NH$_2$;
Heptanoyl-Ser(Bzl)-D-Phe(4'-Cl)-Arg-Tyr(3'-Cl)-Cys-NH$_2$;
Heptanoyl-Ser(Bzl)-D-Phe(4'-Cl)-Arg-Phe(2'-Cl)-Cys-NH$_2$;
Heptanoyl-Ser(Bzl)-D-Phe(4'-Cl)-Arg-Phe(3'-Cl)-Cys-NH$_2$;
Heptanoyl-Ser(Bzl)-D-Phe(4'-Cl)-Arg-Tyr(3',5'-Di-1)-Cys-NH$_2$;
Heptanoyl-Ser(Bzl)-D-Phe(4'-Cl)-Arg-Phe(2'-F)-Cys-NH$_2$;
Heptanoyl-Ser(Bzl)-D-Phe(4'-Cl)-Arg-Phe(3'-F)-Cys-NH$_2$;
Heptanoyl-Ser(Bzl)-D-Phe(4'-Cl)-Arg-Asp(OcHx)-Cys-NH$_2$;
D-Phe(2'-Cl)-Lys-Nal 2'-Cys-NH$_2$;
D-(N-Bzl) Phe(2'-Cl)-Lys-Nal 2'-Cys-NH$_2$;
3'-Cl Phenyl acetyl-Arg-Ala-D-Phe(4'-CF$_3$)-Cys-Trp-NH$_2$;
3'-Br Phenyl acetyl-Arg-Ala-D-Phe(4'-CF$_3$)-Cys-Trp-NH$_2$;
3'-Cl Phenyl acetyl-Arg-Arg-D-Phe(4'-CF$_3$)-Cys-Trp-NH$_2$;
3'-Br Phenyl acetyl-Arg-Arg-D-Phe(4'-CF$_3$)-Cys-Trp-NH$_2$;
Heptanoyl-Ser(Bzl)-D-Phe(2'-Cl)-Lys-Phg-Cys-NH$_2$;
Heptanoyl-Ser(Bzl)-D-Phe(2'-Cl)-Lys-Phe-Cys-NH$_2$;
Heptanoyl-Ser(Bzl)-D-Phe(2'-Cl)-Lys-Hphe-Cys-NH$_2$;
1'-Naphthyl acetyl-Arg-Arg-D-Phe(4'-Cl)-Cys-Trp-NH$_2$;
2'-Naphthyl acetyl-Arg-Arg-D-Phe(4'-Cl)-Cys-Trp-NH$_2$;
1'-Naphthyl acetyl-Arg-Arg-D-Phe(3'-Cl)-Cys-Trp-NH$_2$;
2'-Naphthyl acetyl-Arg-Arg-D-Phe(3'-Cl)-Cys-Trp-NH$_2$;
3'-Br Phenyl acetyl-Arg-Arg-D-Phe(4'-Cl)-Cys-Nal 1'-NH$_2$;
3'-Br Phenyl acetyl-Arg-Arg-D-Phe(4'-Cl)-Cys-Nal 2'-NH$_2$;
3'-Br Phenyl acetyl-Arg-Arg-D-Phe(3'-Cl)-Cys-Nal 1'-NH$_2$;
3'-Br Phenyl acetyl-Arg-Arg-D-Phe(3'-Cl)-Cys-Nal 2'-NH$_2$;
Hept-Ser(Bzl)-D-Phe(4'-Cl)-Arg-D-Trp-Cys-NH$_2$;
Heptanoyl-Ala-Nal 2'-Cys-Trp-NH$_2$; (SEQ ID NO:2)
Heptanoyl-Ser(Bzl)-D-Phe(4'-Cl)-Arg-Hphe-Cys-NH$_2$;
Heptanoyl-Ser(Bzl)-D-Phe(4'-Cl)-Arg-Cys(Bzl)-Cys-NH$_2$;
Heptanoyl-Ser(Bzl)-D-Phe(4'-Cl)-Arg-Tyr(Bzl)-Cys-NH$_2$;
Heptanoyl-Ser(Bzl)-D-Phe(4'-Cl)-Arg-Nal 2'-Cys-Lys-NH$_2$;
Heptanoyl-Ser(Bzl)-D-Phe(2'-Br)-Lys-Nal 2'-Cys-NH$_2$;
Heptanoyl-Ser(Bzl)-D-Phe(2'-F)-Lys-Nal 2'-Cys-NH$_2$;
Ser(Bzl)-D-Phe(2'-Cl)-Lys-Nal 2'-Cys-NH$_2$;
Heptanoyl-D-Hphe-D-Phe(2'-Cl)-Lys-Nal 2'-Cys-NH$_2$;
(N-PhEt)-D-Phe(2'-Cl)-Lys-Nal 2'-Cys-NH$_2$;
Ph(CH$_2$)$_3$-C(O=D)-Phe(2'-Cl)-Lys-Nal 2'-Cys-NH$_2$;
Ph(CH$_2$)$_2$-C(O=D)-Phe(2'-Cl)-Lys-Nal 2'-Cys-NH$_2$;
Ph(CH$_2$)-(C=O)-D-Phe(2'-Cl)-Lys-Nal 2'-Cys-NH$_2$;

Ph-(C=O)-D-Phe(2'-Cl)-Lys-Nal 2'-Cys-NH$_2$;
3'-Br-Phenylacetyl-Arg-Arg-D-Phe(4'-CH$_2$PO$_3$Et$_3$)-Cys-Trp-NH$_2$;
3'-Cl-Phenylacetyl-Arg-Arg-D-Phe(4'-CH$_2$PO$_3$Et$_3$)-Cys-Trp-NH$_2$;
Heptanoyl-Arg-D-Phe-Gly-Trp-Cys-Lys-NH$_2$;
Heptanoyl-Ser(Bzl)-D-Nal 2'-Gly-Trp-Cys-Lys-NH$_2$;
Ac-Nle-Arg-Ala-D-Nal 2'-Cys-Lys-NH$_2$;
Ac-Nle-Arg-Arg-D-Nal 2'-Cys-Lys-NH$_2$;
Ser(Bzl)-D-Phe(4'-Cl)-Arg-Nal 2'-Cys-Lys-NH$_2$;
D-Phe(4'-Cl)-Arg-Nal 2'-Cys-Lys-NH$_2$;
Heptanoyl-Ser(Bzl)-D-Phe(4'-Cl)-Gly-Nal 2'-Cys-Lys-NH$_2$;
Ac-Lys-Ala-D-Phe-D-Cys-Arg-NH$_2$;
Ac-Nle-Ala-D-Phe-D-Cys-Arg-NH$_2$;
Ac-Trp-Ala-D-Phe-D-Cys-Arg-NH$_2$;
Heptanoyl-Ser(Bzl)-D-Phe(4'-Cl)-Arg-Tyr(2',6'-diCl-Bzl)-Cys-NH$_2$;
Heptanoyl-Ser(Bzl)-D-Nal 2'-Arg-Nal 2'-Cys-NH$_2$;
Heptanoyl-Ser(Bzl)-D-Phe(4'-Cl)-Arg-Thr(Bzl)-Cys-NH$_2$;
Heptanoyl-Ser(Bzl)-D-Nal 2'-Arg-Trp-Cys-Lys-NH$_2$;
Heptanoyl-His-D-Phe-Arg-Trp-Cys-Lys-NH$_2$;
Heptanoyl-Pro-D-Phe-Arg-Trp-Cys-Lys-NH$_2$;
Heptanoyl-D-Pro-D-Phe-Arg-Trp-Cys-Lys-NH$_2$;
Heptanoyl-D-Phe-Arg-Trp-Cys-Lys-NH$_2$;
D-Phe-Arg-Trp-Cys-Lys-NH$_2$;
Phe-Arg-Trp-Cys-Lys-NH$_2$; (SEQ ID NO:3)
Phe-Arg-Trp-Cys-Trp-NH$_2$; (SEQ ID NO:4)
D-Phe-Arg-D-Trp-Cys-Trp-NH$_2$;
Phe-Arg-D-Trp-Cys-Lys-NH$_2$;
D-Phe-Arg-D-Trp-Cys-Lys-NH$_2$;
Phe-Arg-D-Trp-Cys-Trp-NH$_2$;
D-Phe-Arg-Trp-D-Cys-Lys-NH$_2$;
Ac-Nle-Ala-His-D-Phe-Arg-Trp-D-Cys-Lys-NH$_2$;
Ac-Lys-Ala-D-Phe-D-Cys-Arg-Trp-NH$_2$;
Ac-Nle-Ala-D-Phe-D-Cys-Arg-Trp-NH$_2$;
Ac-Trp-Ala-D-Phe-D-Cys-Arg-Trp-NH$_2$;
Heptanoyl-Ser(Bzl)-D-Phe(2'-Cl)-Lys-Nal 2'-Cys-NH$_2$;
D-Phe-Arg-Trp-Cys-Trp-NH$_2$;
3'-Br-Phenylacetyl-Lys-Lys-D-Phe(4'-CH$_3$)Cys-Lys-NH$_2$;
3'-Br-Phenylacetyl-Lys-Ala-D-Phe(4'-CH$_3$)Cys-Lys-NH$_2$;
Ac-Nle-Arg-Arg-D-Nal 2'-Cys-Trp-Lys-NH$_2$;
4'-Aminomethyl-Phenylacetyl-Arg-Ala-D-Phe(4'-Cl)-Cys-Trp-NH$_2$;
4'-Aminomethyl-Phenylacetyl-Arg-Arg-D-Phe(4'-Cl)-Cys-Trp-NH$_2$;
D-Phe-Arg-Trp-D-Cys-Trp-NH$_2$;
1-Naphthylacetyl-Arg-Arg-D-Phe(4'-Cl)-Cys-Nal 2'-NH$_2$;
NH$_2$—(CH$_2$)$_6$—CO-Ser(Bzl)-D-Phe(4'-Cl)-Arg-Trp-Cys-NH$_2$;
Ac-Ser(Bzl)-D-Phe(4'-Cl)-Arg-Nal 2'-Cys-NH$_2$;
Ser(Bzl)-D-Phe(4'-Cl)-Arg-Nal 2'-Cys-NH$_2$;
NH$_2$—(CH$_2$)$_6$—CO-Ser(Bzl)-D-Nal 2'-Arg-Nal 2'-Cys-NH$_2$;
Ser(Bzl)-D-Nal 2'-Arg-Nal 2'-Cys-NH$_2$;
Ser(Bzl)-D-Phe(4'-Cl)-Arg-D-Trp-Cys-NH$_2$;
NH$_2$—(CH$_2$)$_6$—CO-Ser(Bzl)-D-Phe(4'-Cl)-Arg-D-Trp-Cys-NH$_2$;
HyP(Bzl)-D-Phe(2'-Cl)-Nal 2'-Cys-NH$_2$;
Ac-His-HyP(Bzl)-D-Phe(2'-Cl)-Arg-Nal 2'-Cys-NH$_2$;
3'-Br Phenyl acetyl-Arg-Arg-D-Bip-Cys-Trp-NH$_2$;
Ac-Nle-Ala-His-D-Bip-Arg-Cys-Trp-NH$_2$;
Ac-Nle-Ala-His-D-Bip-Arg-Cys-Bip-NH$_2$;
3'-Br Phenyl acetyl-Arg-Arg-D-Bip-Cys-Bip-NH$_2$;
3'-Br Phenyl acetyl-Arg-Arg-D-Phe(4'-Cl)-Cys-Bip-NH$_2$;
Ac-Nle-Ala-His-D-Bip-Arg-Trp-Cys-NH$_2$;
Heptanoyl-Ser(Bzl)-D-Bip-Arg-Trp-Cys-NH$_2$;
Ac-Nle-Ala-His-D-Phe-Arg-Bip-Cys-NH$_2$;
Heptanoyl-Ser(Bzl)-D-Phe(4'-Cl)-Arg-Bip-Cys-NH$_2$;
Heptanoyl-Ser(Bzl)-D-Bip-Arg-Bip-Cys-NH$_2$;
Ac-Nle-Ala-His-D-Bip-Arg-Bip-Cys-NH$_2$;
Ac-Nle-Ala-His-D-Phe-Arg-Cys-Bip-NH$_2$;
NH$_2$—(CH$_2$)$_6$—(C=O)-Ser(Bzl)-D-Phe(4'-Cl)-Arg-Trp-Cys-NH$_2$;
3'-Br-Phenylacetyl-His-Gly-D-Phe(4'-Cl)Trp-Cys-NH$_2$;
3'-Br-Phenylacetyl-His-D-Phe(4'-Cl)-Trp-Cys-NH$_2$;
Ac-Ala-Ala-His-D-Phe-Arg-Cys-Trp-NH$_2$;
Ac-Ala-His-D-Phe-Arg-Cys-Trp-NH$_2$;
Ac-Nle-His-D-Phe-Arg-Cys-Trp-NH$_2$;
Ac-Leu-His-D-Phe-Arg-Cys-Trp-NH$_2$;
3'-Phenylpropionyl-His-D-Phe-Arg-Cys-Trp-NH$_2$;
3'-(4'-Hydroxyphenyl)propionyl-His-D-Phe-Arg-Cys-Trp-NH$_2$;
3'-Phenylpropionyl-D-Phe-Arg-Cys-Trp-NH$_2$;
3'-(4'-Hydroxyphenyl)propionyl-D-Phe-Arg-Cys-Trp-NH$_2$;
Naphthlyl-2-acetyl-D-Phe-Arg-Cys-Trp-NH$_2$;
4'-Biphenylacetyl-D-Phe-Arg-Cys-Trp-NH$_2$;
Ac-Nle-Ala-Leu-D-Phe-Arg-Cys-Trp-NH$_2$;
Ac-Nle-Ala-Phe-D-Phe-Arg-Cys-Trp-NH$_2$;
Ac-Nle-Ala-Trp-D-Phe-Arg-Cys-Trp-NH$_2$;
Tic-D-Phe(4'-Cl)-Arg-Trp-Cys-NH$_2$;
Tic-D-Phe(4'-Cl)-Arg-Cys-NH$_2$;
Tic-D-Phe(4'-Cl)-Gln-Cys-NH$_2$;
Tic-D-Phe(4'-Cl)-His-Cys-NH$_2$;
Tic-D-Phe(4'-Cl)-Lys-Cys-NH$_2$;
Ac-Nle-Ala-Tyr-D-Phe-Arg-Cys-Trp-NH$_2$;
Hept-Ser(Bzl)-D-Phe(4'-Cl)-Arg-Trp-Cys-NH$_2$;
NH$_2$(CH$_2$)$_6$—C(=O)-Ser(Bzl)-D-Phe(4'-Cl)-Arg-Trp-Cys-NH$_2$;
NH$_2$(CH$_2$)$_6$—C(=O)-Ser(Bzl)-D-Nal 2'-Arg-Trp-Cys-NH$_2$;
NH$_2$(CH$_2$)$_6$—C(=O)-Ser(Bzl)-D-Nal 2'-Arg-D-Trp-Cys-NH$_2$;
Hept-Ser(Bzl)-D-Nal 2'-Arg-Nal 2'-Cys-NH$_2$;
Tic-D-Phe(2'-Cl)-Arg-Trp-Cys-NH$_2$;
Tic-D-Phe(3'-Cl)-Arg-Trp-Cys-NH$_2$;
Tic-D-Phe-Arg-Trp-Cys-NH$_2$;
Tic-D-Nal-2'-Arg-Trp-Cys-NH$_2$;
Ac-Nle-Ala-D-Tyr-D-Phe-Arg-Cys-Trp-NH$_2$;
Ac-Nle-Ala-Thr-D-Phe-Arg-Cys-Trp-NH$_2$;
Ac-Nle-Ala-Glu-D-Phe-Arg-Cys-Trp-NH$_2$;
Ac-Nle-Ala-Arg-D-Phe-Arg-Cys-Trp-NH$_2$;
Ac-Nle-Ala-Ala-D-Phe-Arg-Cys-Trp-NH$_2$;
Amc-D-Phe-Arg-Cys-Trp-NH$_2$;
D-Pro-D-Phe-Arg-Cys-Trp-NH$_2$;
Idc-D-Phe-Arg-Cys-Trp-NH$_2$;
Pro-D-Phe-Arg-Cys-Trp-NH$_2$;
D-Tiq-D-Phe-Arg-Trp-Cys-NH$_2$;
Tiq-D-Phe-Arg-Trp-Cys-NH$_2$;
1-amino-1-cyclohexane carboxyl-D-Phe-Arg-Trp-Cys-NH$_2$;
1-amino-1-cyclopentane carboxyl-D-Phe-Arg-Trp-Cys-NH$_2$;
Aic-D-Phe-Arg-Trp-Cys-NH$_2$;
Nal 1'-D-Phe-Arg-Trp-Cys-NH$_2$;
D-Nal 1'-D-Phe-Arg-Trp-Cys-NH$_2$;
Nal 2'-D-Phe-Arg-Trp-Cys-NH$_2$;
D-Nal 2'-D-Phe-Arg-Trp-Cys-NH$_2$;
D-Pro-D-Phe-Arg-Trp-Cys-NH$_2$;

Nal 1'-D-Phe-Arg-Cys-Trp-NH$_2$;
Ac-Ala-Ala-Ala-D-Phe-Arg-Cys-Trp-NH$_2$;
Amb-D-Phe-Arg-Cys-Trp-NH$_2$;
D-Nal 1'-D-Phe-Arg-Cys-Trp-NH$_2$;
D-Igl-D-Phe-Arg-Cys-Trp-NH$_2$;
D-Tiq-D-Phe-Arg-Cys-Trp-NH$_2$;
Nal 2'-D-Phe-Arg-Cys-Trp-NH$_2$;
D-Dip-D-Phe-Arg-Cys-Trp-NH$_2$;
allo-Thr-D-Phe-Arg-Cys-Trp-NH$_2$;
D-Nal 2'-D-Phe-Arg-Cys-Trp-NH$_2$;
Igl-D-Phe-Arg-Cys-Trp-NH$_2$;
Igl-D-Phe-Arg-Cys-Trp-NH$_2$;
Tiq-D-Phe-Arg-Cys-Trp-NH$_2$;
Aic-D-Phe-Arg-Cys-Trp-NH$_2$;
1-amino-1-cyclohexane carboxyl-D-Phe-Arg-Cys-Trp-NH$_2$;
1-amino-1-cyclopentane carboxyl-D-Phe-Arg-Cys-Trp-NH$_2$;
Bip-D-Phe-Arg-Trp-Cys-NH$_2$;
4-Amc-D-Phe-Arg-Trp-Cys-NH$_2$;
Idc-D-Phe-Arg-Trp-Cys-NH$_2$;
Amb-D-Phe-Arg-Trp-Cys-NH$_2$;
Pro-D-Phe-Arg-Trp-Cys-NH$_2$;
D-Igl-D-Phe-Arg-Trp-Cys-NH$_2$;
Igl-D-Phe-Arg-Trp-Cys-NH$_2$;
Z-D-Pyr-D-Phe-Arg-Trp-Cys-NH$_2$;
D-Dip-D-Phe-Arg-Trp-Cys-NH$_2$;
Allo-Thr-D-Phe-Arg-Trp-Cys-NH$_2$;
D-Igl-D-Nal 2'-Arg-Cys-NH$_2$;
7-amino-haptanoyl-D-Igl-D-Phe-Arg-Cys-NH$_2$;
7-amino-haptanoyl-Ser(Bzl)-D-Nal 2'-Arg-Cys-NH$_2$;
7-amino-Heptanoyl-D-Igl-D-Phe-Arg-Trp-Cys-NH$_2$;
D-Igl-D-Nal 2'-Arg-Trp-Cys-NH$_2$;
Ser(Bzl)-D-Phe-Arg-Trp-Cys-NH$_2$;
3'-Bromo phenyl acetyl-Arg-His-D-Phe(4'-Cl)-Cys-NH$_2$;
3'-Bromo phenyl acetyl-Arg-Ala-D-Phe(4'-Cl)-Cys-NH$_2$;
3'-Bromo phenyl acetyl-Arg-Trp-D-Phe(4'-Cl)-Cys-NH$_2$;
3'-Bromo phenyl acetyl-Arg-Thr-D-Phe(4'-Cl)-Cys-NH$_2$;
3'-Bromo phenyl acetyl-Arg-Thr(Bzl)-D-Phe(4'-Cl)-Cys-NH$_2$;
3'-Bromo phenyl acetyl-Arg-Ala-D-Phe(4'-Cl)-Cys-Trp-NH$_2$;
3'-Bromo phenyl acetyl-Lys-Ala-D-Phe(4'-Me)-Cys-Trp-NH$_2$;
3'-Bromo phenyl acetyl-Lys-Ala-D-Phe(3'-Cl)-Cys-Trp-NH$_2$;
3'-Bromo phenyl acetyl-Arg-Arg-D-Phe(4'-Cl)-Cys-Trp-NH$_2$;
3'-Bromo phenyl acetyl-Arg-Arg-D-Phe(4'-Cl)-Cys-Nal 2'-NH$_2$;
Ac-Nle-Ala-His-D-Phe-Arg-Nal 2'-Cys-NH$_2$;
Ac-Nle-Ala-His-D-Phe-Arg-D-Nal 2'-Cys-NH$_2$;
Ac-Nle-Ala-His-D-Phe-Arg-Nal 1'-Cys-NH$_2$;
Ac-Nle-Ala-His-D-Phe-Arg-D-Nal 1'-Cys-NH$_2$;
Ac-Nle-Ala-His-D-Phe-Arg-Trp-Cys-NH$_2$;
3'-Br Phenyl acetyl-Arg-Arg-D-Phe(4'-Cl)-Cys-Trp-Nh$_2$;
Ac-Nle-Ala-His-D-Phe-(3'-Cl)-Arg-D-Trp-Cys-Trp-NH$_2$;
3-Br Phenyl acetyl-Arg-Arg-D-Phe(4'-Cl)-Cys-Trp-NH$_2$;
Heptanoyl-Ser(Bzl)-D-Nal 2'-Arg-D-Trp-Cys-NH$_2$;
Ac-Nle-Ala-His-D-Phe-Arg-His-Cys-NH$_2$; and
Ac-Nle-Ala-His-D-Phe-Arg-D-His-Cys-NH$_2$.

11. The peptide of claim 5 or the metallopeptide of claim 10 wherein said metal ion comprises a rhenium ion.

12. The peptide or salt thereof of claim 1 wherein the said metal ion is a rhenium ion.

* * * * *